(12) United States Patent
Li et al.

(10) Patent No.: US 7,767,674 B2
(45) Date of Patent: Aug. 3, 2010

(54) KINASE INHIBITORS

(75) Inventors: Tiechao Li, Fishers, IN (US); Mark Andrew Pobanz, Westfield, IN (US); Chuan Shih, Carmel, IN (US); Yong Wang, Carmel, IN (US); Boyu Zhong, Carmel, IN (US); Jesus Andres Blas, Madrid (ES); Alfonso De Dios, Madrid (ES); Beatriz Lopez De Uralde-Garmendia, Madrid (ES); Luisa Maria Martin Cabrejas, Madrid (ES)

(73) Assignee: Eli Lilly and Company, Indianapolis, IN (US)

( * ) Notice: Subject to any disclaimer, the term of this patent is extended or adjusted under 35 U.S.C. 154(b) by 639 days.

(21) Appl. No.: 11/569,809

(22) PCT Filed: Jun. 15, 2005

(86) PCT No.: PCT/US2005/021148

§ 371 (c)(1),
(2), (4) Date: Nov. 30, 2006

(87) PCT Pub. No.: WO2006/009741

PCT Pub. Date: Jan. 26, 2006

(65) Prior Publication Data

US 2008/0306068 A1    Dec. 11, 2008

Related U.S. Application Data

(60) Provisional application No. 60/592,539, filed on Jul. 30, 2004, provisional application No. 60/622,492, filed on Oct. 27, 2004.

(30) Foreign Application Priority Data

Jun. 23, 2004    (EP) .................................. 04380131
Aug. 23, 2004    (EP) .................................. 04380174

(51) Int. Cl.
*A61K 31/5377*    (2006.01)
*A61K 31/496*    (2006.01)
*A61K 31/415*    (2006.01)
*A61K 31/4439*    (2006.01)
*C07D 231/40*    (2006.01)
*C07D 401/12*    (2006.01)
*C07D 413/14*    (2006.01)

(52) U.S. Cl. ............................. 514/236.5; 514/253.09; 514/254.05; 514/326; 544/129; 544/364; 544/370; 546/211

(58) Field of Classification Search ...................... None
See application file for complete search history.

(56) References Cited

U.S. PATENT DOCUMENTS

2007/0010529 A1*    1/2007    Takahashi et al. ...... 514/254.05

FOREIGN PATENT DOCUMENTS

| WO | WO 00/43384 | 7/2000 |
| WO | WO 00/55139 | 9/2000 |
| WO | WO 03/072569 | 9/2003 |
| WO | WO 2004/100946 | 11/2004 |
| WO | WO 2004/101529 | 11/2004 |

OTHER PUBLICATIONS

Lee et al. Immunopharmacology, vol. 47, p. 185-201 (2000).*
Mayer et al. Drug Discovery Today, vol. 3, p. 49-54 (2006).*

* cited by examiner

*Primary Examiner*—Emily Bernhardt
(74) *Attorney, Agent, or Firm*—Tina M. Tucker

(57) ABSTRACT

The present invention provides kinase inhibitors of Formula I:

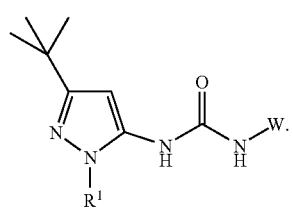

I

3 Claims, No Drawings

KINASE INHIBITORS

This is the national phase application, under 35 USC 371, for PCT/US2005/021148, filed 15 Jun. 2005, which, claims the benefit, under 35 USC 119(e), of GB provisional application 04380131.5 filed 23 Jun. 2004, U.S. provisional application 60/592,539 filed 30 Jul. 2004, GB provisional application 04380174.5 filed 23 Aug. 2004, and U.S. provisional application 60/622,492 filed 27 Oct. 2004.

BACKGROUND OF THE INVENTION

The p38 kinase is a mitogen-activated protein (MAP) kinase that belongs to the serine/threonine kinase superfamily. This kinase is activated by extracellular stresses such as heat, UV light, and osmotic stress, as well as by inflammatory stimuli such as lipopolysaccharide. When activated, p38 kinase phosphorylates intracellular protein substrates that regulate the biosynthesis of the pro-inflammatory cytokines tumor necrosis factor α (TNF-α) and interleukin-β (IL-1β). These cytokines are implicated in the pathology of a number of chronic inflammatory disorders (Lee, et al., *Ann. N.Y. Acad. Sci.*, 696, 149-170 (1993); Muller-Ladner, *Curr. Opin. Rheumatol.*, 8, 210-220 (1996)), cardiovascular and central nervous system disorders (Salituro, et al., *Current Medicinal Chemistry*, 6, 807-823 (1999)), and autoimmune disorders (Pargellis, et al., *Nature Structural Biology*, 9(4), 268-272 (2002)).

A number of urea compounds (for example, WO 9923091, WO 01012188, WO 04004720, WO 04037789, WO 99/32111, US 2004/0058961, WO 2004/100946, and WO 0043384) have been identified as p38 kinase inhibitors or cytokine inhibitors. However, there remains a need for treatment in this field for compounds that are cytokine suppressive drugs, i.e., compounds that are capable of inhibiting p38 kinase.

The present invention provides new inhibitors of p38 kinase useful for the treatment of conditions resulting from excessive cytokine production.

BRIEF SUMMARY OF THE INVENTION

The present invention provides compounds of Formula I:

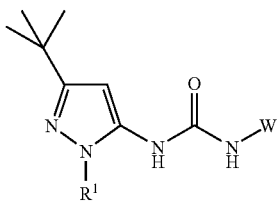

wherein:
$R^1$ is hydrogen, $C_1$-$C_4$ alkyl, or tolyl;
W is 1-(4-methylsulfonylbenzoyl)-piperidin-4-yl-, [1-(2,6-dichlorobenzoyl)-piperidin-4-yloxy]naphthyl-, [1-(2,6-dichlorobenzoyl)-piperidin-4-yl]-($C_1$-$C_2$ alkoxy)-naphthyl-, [1-(2,6-dichlorobenzoyl)-piperidin-4-yl]-phenyl-, (1-Y-piperidin-4-yloxy)-phenyl-, [1-(2,6-dichlorobenzoyl)-piperazin-4-yl]-methyl-phenyl-, (1-Y-piperazin-4-yl)-methyl-phenyl-, (1-Y-piperazin-4-yl)-phenyl-, or 4-[1-(pyridin-4-ylmethyl)-piperazin-4-ylcarbonyl]-phenyl- wherein phenyl is optionally substituted with one to two substituents from the group consisting of halo, methyl, and trifluoromethyl;

Y is —C(O)—$R^2$, $C_1$-$C_3$ alkylsulfonyl, or cyclopropylsulfonyl; and
$R^2$ is $C_1$-$C_6$ alkyl, $C_1$-$C_6$ alkoxy, $C_1$-$C_6$ alkoxy-($C_1$-$C_6$ alkyl), amino, benzyloxy, indolyl, tetrahydrofuryl, piperidinyl, trichloromethyl, cyclopentylmethyl; $C_3$-$C_5$ cycloalkyl optionally substituted with 1-3 substituents independently selected from the group consisting of phenyl, $C_1$-$C_4$ alkyl, and halo, pyridinyl optionally substituted with 1-2 substituents independently selected from the group consisting of $C_1$-$C_4$ alkoxy and halo, thienyl optionally substituted with 1-2 halo or $C_1$-$C_4$ alkyl substituents, pyrrolyl optionally substituted with 1-2 $C_1$-$C_4$ alkyl substituents, imidazolyl, pyrazolyl optionally substituted with 1-3 $C_1$-$C_4$ alkyl substituents, or phenyl optionally substituted with 1-2 substituents independently selected from the group consisting of halo, trifluoromethyl, trifluoromethoxy, $C_1$-$C_4$ alkoxy, 4-methylpiperazin-1-ylmethyl, 2-(dimethylamino)ethoxy, and morpholin-4-ylmethyl;

or a pharmaceutically acceptable salt thereof.

The present invention provides a method of inhibiting p-38 kinase in a mammal comprising administering to a mammal in need of such treatment an effective amount of a compound of Formula I or a pharmaceutically acceptable salt thereof.

The present invention also provides a method of suppressing the production of tumor necrosis factor α (TNF-α) in a mammal comprising administering to a mammal in need of such treatment an effective amount of a compound of Formula I or a pharmaceutically acceptable salt thereof.

The present invention also provides a method of suppressing the production of interleukin-β (IL-1β) in a mammal comprising administering to a mammal in need of such treatment an effective amount of a compound of Formula I or a pharmaceutically acceptable salt thereof.

The present invention further provides a method of treating conditions resulting from excessive cytokine production in a mammal comprising administering to a mammal in need of such treatment a cytokine-suppressing amount of a compound of Formula I or a pharmaceutically acceptable salt thereof.

The present invention also provides a method of inhibiting the growth of a susceptible neoplasm in a mammal comprising administering to a mammal in need of such treatment a p38 inhibiting amount of a compound of Formula I or a pharmaceutically acceptable salt thereof.

The present invention also provides a method of inhibiting metastasis in a mammal comprising administering to a mammal in need of such treatment a p38 inhibiting amount of a compound of Formula I or a pharmaceutically acceptable salt thereof.

The present invention also provides a method of treating rheumatoid arthritis in a mammal comprising administering to a mammal in need of such treatment a p38 inhibiting amount of a compound of Formula I or a pharmaceutically acceptable salt thereof.

The present invention also provides a pharmaceutical formulation comprising a compound of Formula I or a pharmaceutically acceptable salt thereof, in combination with a pharmaceutically acceptable excipient, carrier, or diluent.

This invention also provides the use of a compound of Formula I or a pharmaceutically acceptable salt thereof for the manufacture of a medicament for the inhibition of p38 kinase. Additionally, this invention provides a compound of Formula I or a pharmaceutically acceptable salt thereof for use in the inhibition of p38 kinase in mammals. Furthermore, this invention provides a pharmaceutical composition adapted for the inhibition of p38 kinase comprising a compound of Formula I or a pharmaceutically acceptable salt thereof in combination with one or more pharmaceutically acceptable excipients, carriers, or diluents thereof.

This invention also provides the use of a compound of Formula I or a pharmaceutically acceptable salt thereof for the manufacture of a medicament for the suppression of the production of tumor necrosis factor α (TNF-α). Additionally, this invention provides a compound of Formula I or a pharmaceutically acceptable salt thereof for use in the suppression of the production of tumor necrosis factor α (TNF-α) in mammals. Furthermore, this invention provides a pharmaceutical composition adapted for the suppression of the production of tumor necrosis factor α (TNF-α) comprising a compound of Formula I or a pharmaceutically acceptable salt thereof in combination with one or more pharmaceutically acceptable excipients, carriers, or diluents.

This invention also provides the use of a compound of Formula I or a pharmaceutically acceptable salt thereof for the manufacture of a medicament for the suppression of the production of interleukin-1β (IL-1β). Additionally, this invention provides a compound of Formula I or a pharmaceutically acceptable salt thereof for use in the suppression of the production of interleukin-1β (IL-1β) in mammals. Furthermore, this invention provides a pharmaceutical composition adapted for the suppression of the production of interleukin-1β (IL-1β) comprising a compound of Formula I, or a pharmaceutically acceptable salt thereof, in combination with one or more pharmaceutically acceptable excipients, carriers, or diluents.

This invention also provides the use of a compound of Formula I or a pharmaceutically acceptable salt thereof for the manufacture of a medicament for the treatment of conditions resulting from excessive cytokine production. Additionally, this invention provides a compound of Formula I or a pharmaceutically acceptable salt thereof for use in the treatment of conditions resulting from excessive cytokine production in mammals. Furthermore, this invention provides a pharmaceutical composition adapted for the treatment of conditions resulting from excessive cytokine production comprising a compound of Formula I or a pharmaceutically acceptable salt thereof in combination with one or more pharmaceutically acceptable excipients, carriers, or diluents.

This invention also provides the use of a compound of Formula I or a pharmaceutically acceptable salt thereof for the manufacture of a medicament for the inhibition of growth of a susceptible neoplasm. Additionally, this invention provides a compound of Formula I or a pharmaceutically acceptable salt thereof for use in the inhibition of growth of a susceptible neoplasm in mammals. Furthermore, this invention provides a pharmaceutical composition adapted for the inhibition of growth of a susceptible neoplasm comprising a compound of Formula I or a pharmaceutically acceptable salt thereof in combination with one or more pharmaceutically acceptable excipients, carriers, or diluents.

This invention also provides the use of a compound of Formula I or a pharmaceutically acceptable salt thereof for the manufacture of a medicament for the inhibition of metastasis. Additionally, this invention provides a compound of Formula I or a pharmaceutically acceptable salt thereof for use in the inhibition of metastasis in mammals. Furthermore, this invention provides a pharmaceutical composition adapted for the inhibition of metastasis comprising a compound of Formula I or a pharmaceutically acceptable salt thereof in combination with one or more pharmaceutically acceptable excipients, carriers, or diluents.

This invention also provides the use of a compound of Formula I or a pharmaceutically acceptable salt thereof for the manufacture of a medicament for the treatment of rheumatoid arthritis. Additionally, this invention provides a compound of Formula I or a pharmaceutically acceptable salt thereof for use in the treatment of rheumatoid arthritis in mammals. Furthermore, this invention provides a pharmaceutical composition adapted for the treatment of rheumatoid arthritis comprising a compound of Formula I or a pharmaceutically acceptable salt thereof in combination with one or more pharmaceutically acceptable excipients, carriers, or diluents.

DETAILED DESCRIPTION OF THE INVENTION

The general chemical terms used in the formulae above have their usual meanings. For example, the term "$C_1$-$C_6$ alkyl" includes straight chain and branched alkyls, e.g., methyl, ethyl, propyl, isopropyl, butyl, isobutyl, sec-butyl, tert-butyl, pentyl, and hexyl moieties. The term "$C_1$-$C_4$ alkyl" is included within the meaning of the term "$C_1$-$C_6$ alkyl" and includes methyl, ethyl, propyl, isopropyl, butyl, isobutyl, sec-butyl, and tert-butyl. The term "$C_1$-$C_6$ alkoxy" includes methoxy, ethoxy, propoxy, butoxy, pentoxy, and hexoxy. The term "$C_1$-$C_4$ alkoxy" includes methoxy, ethoxy, propoxy, and butoxy. The term "$C_1$-$C_6$ alkoxy-($C_1$-$C_6$ alkyl)" refers to an alkoxy group attached through an alkylene linker. The term "$C_1$-$C_3$ alkylsulfonyl" refers to a sulfonyl group that is substituted with a methyl, ethyl, or propyl group. The term "$C_3$-$C_5$ cycloalkyl" includes cyclopropyl, cyclobutyl, and cyclopentyl moieties. The term "halo" includes fluoro, chloro, bromo, and iodo.

The term "p-38 kinase" is taken to mean the p-38a and/or p-38α kinase isoforms.

The term "suppressing the production of TNF-α (IL-1β, cytokine)" is taken to mean decreasing of excessive in vivo levels of TNF-α, IL-1β, or another cytokine in a mammal to normal or sub-normal levels. This may be accomplished by inhibition of the in vivo release of TNF-α, IL-1β, or another cytokine by all cells, including macrophages; by down regulation, at the genomic level, of excessive in vivo levels of TNF-α, IL-1β, or another cytokine in a mammal to normal or sub-normal levels; by inhibition of the synthesis of TNF-α, IL-1β, or another cytokine as a posttranslational event; or by a down regulation of TNF-α, IL-1β, or another cytokine at the translational level.

The skilled artisan will appreciate that certain compounds of Formula I contain at least one chiral center. The present invention contemplates all individual enantiomers or diastereomers, as well as mixtures of the enantiomers and diastereomers of said compounds including racemates. It is preferred that compounds of Formula I containing at least one chiral center exist as single enantiomers or diastereomers. The single enantiomers or diastereomers may be prepared beginning with chiral reagents or by stereoselective or stereospecific synthetic techniques. Alternatively, the single enantiomers or diastereomers may be isolated from mixtures by standard chiral chromatographic or crystallization techniques.

It will be understood by the skilled reader that most or all of the compounds of the present invention are capable of forming salts. In all cases, the pharmaceutically acceptable salts of all of the compounds are included in the names of them. The compounds of the present invention are amines, and accordingly react with any of a number of inorganic and organic acids to form pharmaceutically acceptable acid addition salts. Preferred pharmaceutically acceptable salts are those formed with hydrochloric acid and methanesulfonic acid.

While all of the compounds of Formula I are useful inhibitors of p-38 kinase, certain classes of compounds are preferred. The following paragraphs describe such preferred classes:

a) W is [1-(2,6-dichlorobenzoyl)-piperidin-4-yl]-phenyl-, (1-Y-piperazin-4-yl)-phenyl-, or (1-Y-piperidin-4-yloxy)-phenylb) Y is C(O)—R²;
c) R¹ is methyl;
d) R¹ is tolyl;
e) R² is phenyl substituted 1-2 times with halo;
f) R² is tert-butyl;
g) R² is cyclopropyl;

Preferred embodiments of the present invention include all combinations of paragraphs a)-g).

The compounds of Formula I are inhibitors of p38 kinase. Thus, the present invention also provides a method of inhibiting p38 kinase in a mammal that comprises administering to a mammal in need of said treatment a p38 kinase-inhibiting amount of a compound of Formula I. It is preferred that the mammal to be treated by the administration of the compounds of Formula I is human.

As inhibitors of p38 kinase, the compounds of the present invention are useful for suppressing the production of the pro-inflammatory cytokines tumor necrosis factor α (TNF-α) and interleukin-1β (IL-1β), and therefore for the treatment of disorders resulting from excessive cytokine production. The present compounds are therefore believed to be useful in treating inflammatory disorders, including eczema, atopic dermatitis, rheumatoid arthritis, osteoarthritis, inflammatory bowel disease, and toxic shock syndrome. The compounds of the present invention are also believed to be useful in the treatment of cardiovascular disorders, such as acute myocardial infarction, chronic heart failure, atherosclerosis, viral myocarditis, cardiac allograft rejection, and sepsis-associated cardiac dysfunction. Furthermore, the compounds of the present invention are also believed to be useful for the treatment of central nervous system disorders, such as meningococcal meningitis, Alzheimer's disease, Parkinson's disease, and multiple sclerosis.

Most solid tumors increase in mass through the proliferation of malignant cells and stromal cells, including endothelial cells. In order for a tumor to grow larger than 2-3 millimeters in diameter, it must form a vasculature, a process known as angiogenesis. Suppression of tumor-induced angiogenesis by angiostatin and endostatin has been reported to result in antitumor activity (O'Reilly, et al., *Cell*, 88, 277-285 (1997)). The selective p38 kinase inhibitor SB22025 has been shown to inhibit angiogenesis (J. R. Jackson, et al., *J. Pharmacol. Exp. Therapeutics*, 284, 687 (1998)). Because angiogenesis is a critical component of the mass expansion of most solid tumors, the development of new p38 kinase inhibitors for the inhibition of this process represents a promising approach for antitumor therapy. This approach to antitumor therapy may lack the toxic side effects or drug resistance-inducing properties of conventional chemotherapy (Judah Folkman, *Endogenous Inhibitors of Angiogenesis*, The Harvey Lectures, Series 92, pages 65-82, Wiley-Liss Inc., (1998)).

As inhibitors of p38 kinase, the compounds of the present invention, therefore, are also useful in inhibiting growth of susceptible neoplasms. Schultz, R. M. *Potential of p38 MAP kinase inhibitors in the treatment of cancer*. In: E. Jucker (ed.), *Progress in Drug Research*, 60, 59-92, (2003). A susceptible neoplasm is defined to be a neoplasm that depends upon p38 kinase for its survival, growth, or metastasis. Susceptible neoplasms include tumors of the brain, genitourinary tract, lymphatic system, stomach, larynx, and lung (U.S. Pat. No. 5,717,100). Preferably, the term "susceptible neoplasms" as used in the present application includes human cancers including non-small cell lung carcinoma (A. Greenberg, et al., *Am. J. Respir. Cell Mol. Biol.*, 26, 558 (2002)), breast carcinoma (J. Chen, et al., *J. Biol. Chem.*, 276, 47901 (2001); B. Salh, et al., *Int. J. Cancer*, 98, 148 (2002); and S. Xiong, et al., *Cancer Res.*, 61, 1727 (2001)), gastric carcinoma (Y. D. Jung, et al., *Proc. Am. Assoc. Cancer Res.*, 43, 9 (2002)), colorectal carcinomas (S. Xiong, et al., *Cancer Res.*, 61, 1727 (2001)), and malignant melanoma (C. Denkert, et al., *Clin. Exp. Metastasis*, 19, 79 (2002)).

Inhibition of angiogenesis by suppression of TNF-α has also been taught to be useful in the inhibition or prevention of metastasis (U.S. Pat. No. 6,414,150; U.S. Pat. No. 6,335,336). Furthermore, suppression of TNF-α is indicated for the treatment and prevention of cachexia, a wasting syndrome experienced by about half of all cancer patients (T. Yoneda, et al., *J. Clin. Invest.*, 87, 977 (1991)).

Furthermore, inhibition of p38 kinase may be effective in the treatment of certain viral conditions such as influenza (K. Kujime, et al., *J. Immunology.*, 164, 3222-3228 (2000)), rhinovirus (S. Griego, et al., *J. Immunology*, 165, 5211-5220 (2000)), and HIV (L. Shapiro, et al., *Proc. Natl. Acad. Sci. USA*, 95, 7422-7426, (1998)).

The compounds of the present invention can be prepared by a variety of procedures, some of which are illustrated in the Schemes below. It will be recognized by one of skill in the art that the individual steps in the following schemes may be varied to provide the compounds of Formula I. The particular order of steps required to produce the compounds of Formula I is dependent upon the particular compound being synthesized, the starting compound, and the relative lability of the substituted moieties. Some substituents have been eliminated in the following schemes for the sake of clarity and are not intended to limit the teaching of the schemes in any way.

SCHEMES

Formula I (i)

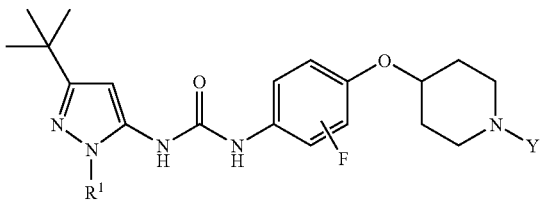

Formula I (ii)

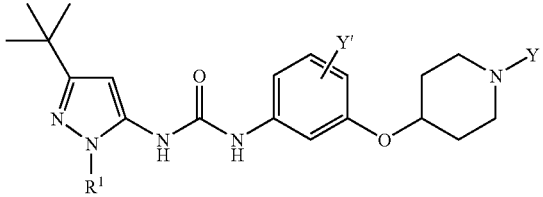

Y' is H, F, CF₃, or CH₃

Formula I (iii)

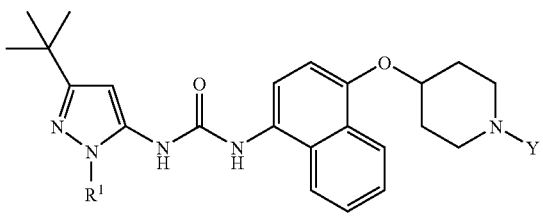

-continued

Formula (iv)

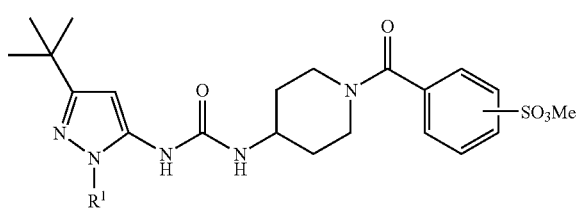

Formula I (v)

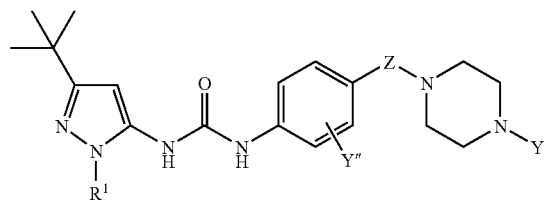

Z is CH₃, C=O, bond
Y″ is H,F

Formula I (vi)

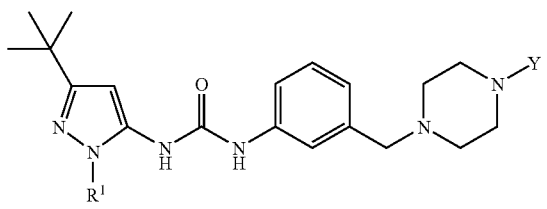

p-Fluoronitrobenzene (a) is reacted with an N-protected (PG) hydroxypiperidine, an alkali hydroxide, and a tetraalkylammonium salt as phase transfer catalyst in a polar protic solvent, preferably water, to provide the corresponding nitrophenyl substituted piperidine (b) (Methods for introducing and removing nitrogen protecting groups are well known in the art; see, for example, Greene and Wuts, Protective Groups in Organic Synthesis, 3rd Ed., John Wiley and Sons, New York, Chapter 7 (1999)). The nitro moiety is reduced with hydrogen or reducing agents, e.g., palladium catalysis, hydrogen, in a suitable solvent such as lower alkanols to provide the corresponding amine (c). This amine is then reacted with an appropriate pyrazolyl-2,2,2-trichloroethyl carbamate to provide an N-protected-piperidine substituted urea (d). After deprotection, the procedure provides the substituted piperidine (e). Finally, the substituted piperidine (e) is reacted with a substituted carboxylic acid under the standard coupling conditions for organic acids and organic amines in the presence of a dehydrating or coupling agent, such as, a carbonyl diimidazole; or with a substituted acid chloride or sulfonyl chloride and a base scavenger to provide Formula I (i). Furthermore, piperidine (e) may be alkylated with e.g., methyliodide in the presence of a base scavenger [March, *Advanced Organic Chemistry*, 5$^{th}$ Ed., John Wiley and Sons, New York (2001)] to provide Formula I (i). The skilled artisan will appreciate that examples of Formula I may be prepared by 1) beginning with other fluoronitrobenzene isomers; 2) beginning with other protected piperidine isomers, including different N-protecting groups which may require other deprotection procedures to form intermediate (e); and 3) reacting amine (c) with other reactive carbamates or isocyanates.

Scheme 1

Compounds of Formula I(i), may be prepared as illustrated in the following Scheme where R¹ is as previously defined:

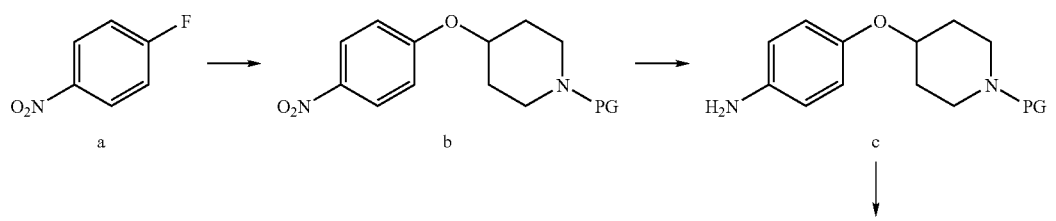

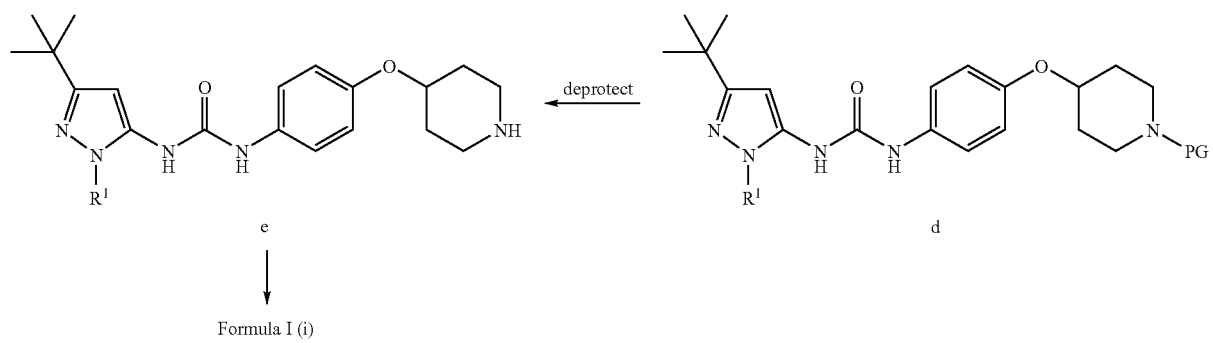

Scheme 2

Compounds of Formula I (ii) may be prepared as illustrated in the following Scheme where $R^1$ is as previously defined.

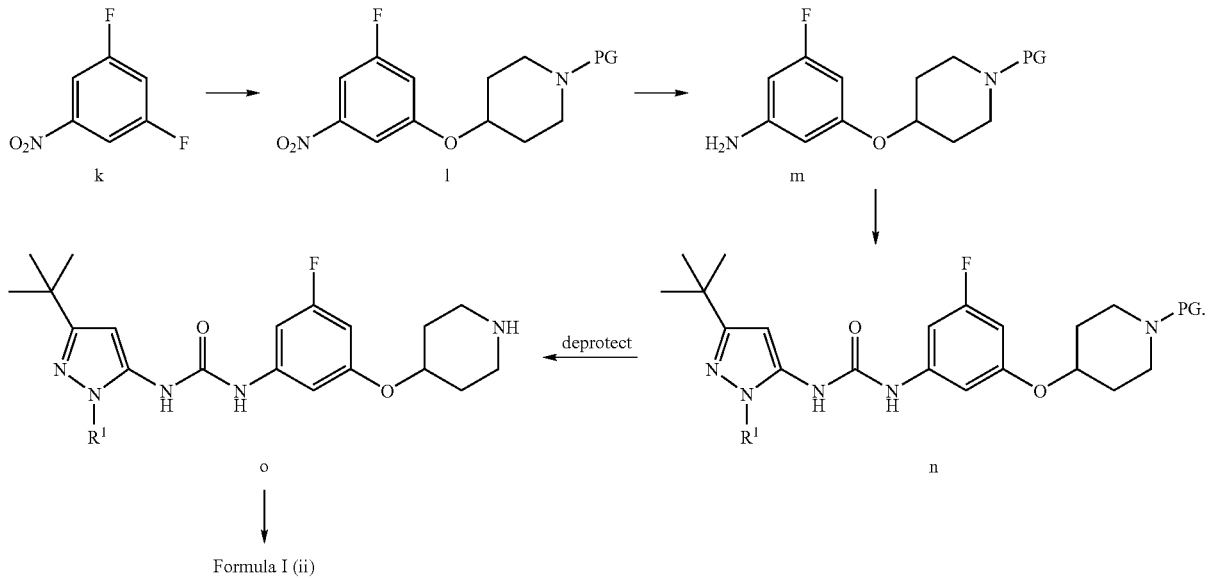

1,3-Difluoronitrobenzene (k) is reacted with an N-protected (PG) hydroxypiperidine, an alkali hydroxide, and a tetraalkylammonium salt as phase transfer catalyst in a polar protic solvent, preferably water, to provide the corresponding nitrophenyl substituted piperidine (l). The nitro moiety is reduced with hydrogen or reducing agents, e.g., palladium catalysis, hydrogen, in a suitable solvent such as lower alkanols to provide the corresponding amine (m). This amine is then reacted with an appropriate pyrazolyl-2,2,2-trichloroethyl carbamate to provide an N-protected-piperidine substituted urea (n). After deprotection, the procedure provides the substituted piperidine (o). Finally, the substituted piperidine (o) is reacted with a substituted carboxylic acid under the standard coupling conditions for organic acids and organic amines in the presence of a dehydrating or coupling agent, such as, a carbonyl di-imidazole; or with a substituted acid chloride or sulfonyl chloride and a base scavenger to provide Formula I (ii). The skilled artisan will appreciate that examples of Formula I may be prepared by 1) beginning with other fluoronitrobenzene isomers of intermediate (k); 2) beginning with other protected piperidine isomers; and 3) reacting amine (m) with other active carbamates or isocyanates.

Scheme 3

Compounds of Formula I (i, ii, and iii) may also be prepared as illustrated in the following Scheme where Z is as previously defined:

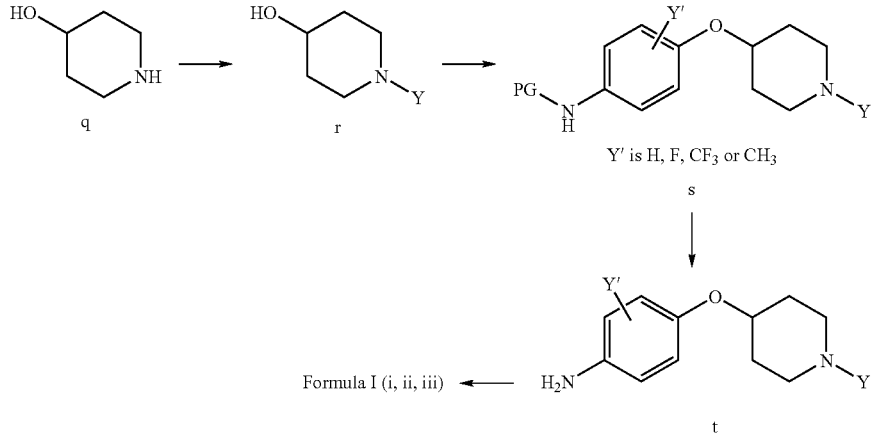

A hydroxypiperidine (q) is reacted with an appropriately substituted carboxylic acid chloride, sulfonyl chloride, or protecting group, e.g., benzyloxychlorocarbonyl in a suitable solvent such as methylene chloride and organic base such as triethylamine to provide the corresponding N-substituted hydroxypiperidine (r). The substituted piperidine (r) is treated with an N-protected amino-phenol or an N-protected amino-naphthol under Mitsunobu conditions [March, *Advanced Organic Chemistry*, 5$^{th}$ Ed., John Wiley and Sons, New York (2001)] to provide the corresponding phenyl ether (s). After selective deprotection of the aniline fragment, the procedure provides the amine (t). Finally, the amine is reacted with an appropriate pyrazolyl isocyanate or carbamic acid, 222-trichloroethyl ester to provide Formula I (i, ii. iii). The skilled artisan will appreciate that examples of Formula I (i, ii, and iii) may be prepared by 1) beginning with other piperidine isomers of intermediate (q); and 2) using other isomers of aminophenol(s) or aminonaphthol(s) to form phenyl or naphthylethers.

Scheme 4

Compounds of Formula I (iv) may be prepared as illustrated in the following Scheme where Y is defined as before:

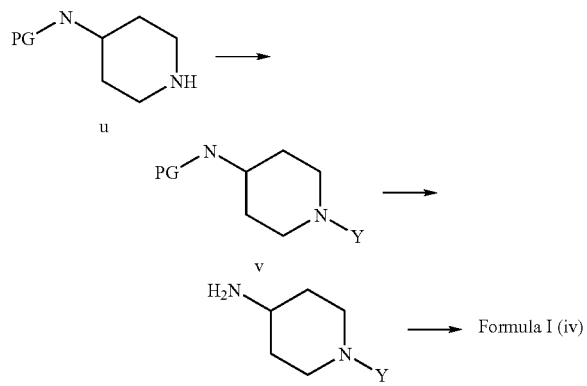

An N-protected amino-piperidine (u) is reacted with a substituted carboxylic acid under the standard coupling conditions for organic acids and organic amines in the presence of a dehydrating or coupling agent, such as, a carbonyl diimidazole to give the ring nitrogen substituted piperidine (v). After deprotection, the procedure provides the amine (w). Finally, the amine is reacted with an appropriate pyrazolyl isocyanate or carbamic acid, 222-trichloroethyl ester to provide I (iv). The skilled artisan will appreciate that examples of Formula I may be prepared by beginning with other piperidine isomers of intermediate (u).

Scheme 5

Compounds of Formula I (v, Z is CH$_2$, C═O) and Formula I (vi) may be prepared as illustrated in the following Scheme where R$^1$ is defined as before:

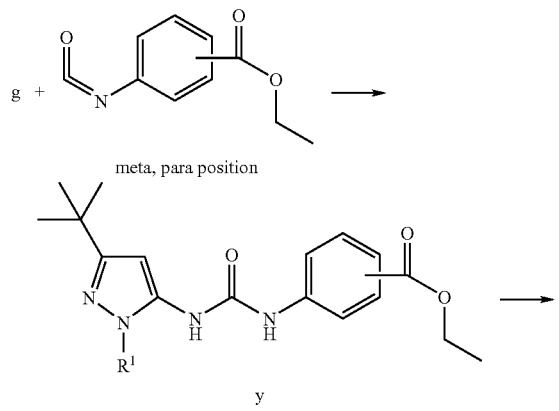

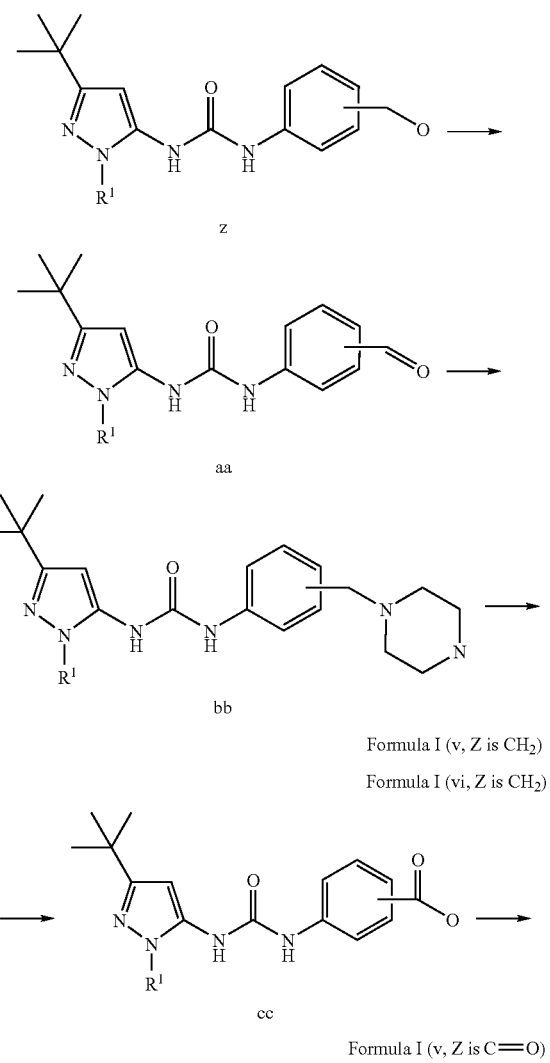

Formula I (v, Z is CH$_2$)

Formula I (vi, Z is CH$_2$)

Formula I (v, Z is C═O)

The intermediate (y), prepared from (g) and an isocyanatobenzoic acid ethyl ester, is reduced in a suitable solvent such as THF with DIBAL to give the benzyl alcohol (z). The benzyl alcohol is oxidized to the aldehyde (aa) with, e.g., MnO$_2$ in methylene chloride. The carboxaldehyde is treated with piperazine under reducing conditions, e.g., with sodium borohydride in methylene chloride to give the amine (bb), which is reacted with a substituted carboxylic acid under the standard coupling conditions for organic acids and organic amines in the presence of a dehydrating or coupling agent, such as, a carbonyl diimidazole to give Formula I (v, vi). The skilled artisan will appreciate that examples of Formula I may be prepared by 1) beginning with other ureas or urea isomers of intermediate (y); 2) using other reducing conditions, e.g., catalytic hydrogenation, to form (z); and 3) using other oxidation conditions, e.g., Swern conditions when appropriate to form (aa).

Alternately, the ester fragment of intermediate (y) may be saponified, with alkali hydroxide in a lower alkanol to the acid (cc), and the acid is reacted with a mono-substituted piperazine in the presence of a dehydrating or coupling agent, such as, a carbonyl diimidazole to give Formula I (v).

Scheme 6

Compounds of Formula I (v, Z is CH$_2$, Y" is H) may be prepared as illustrated in the following Scheme where R$^1$ is defined as before:

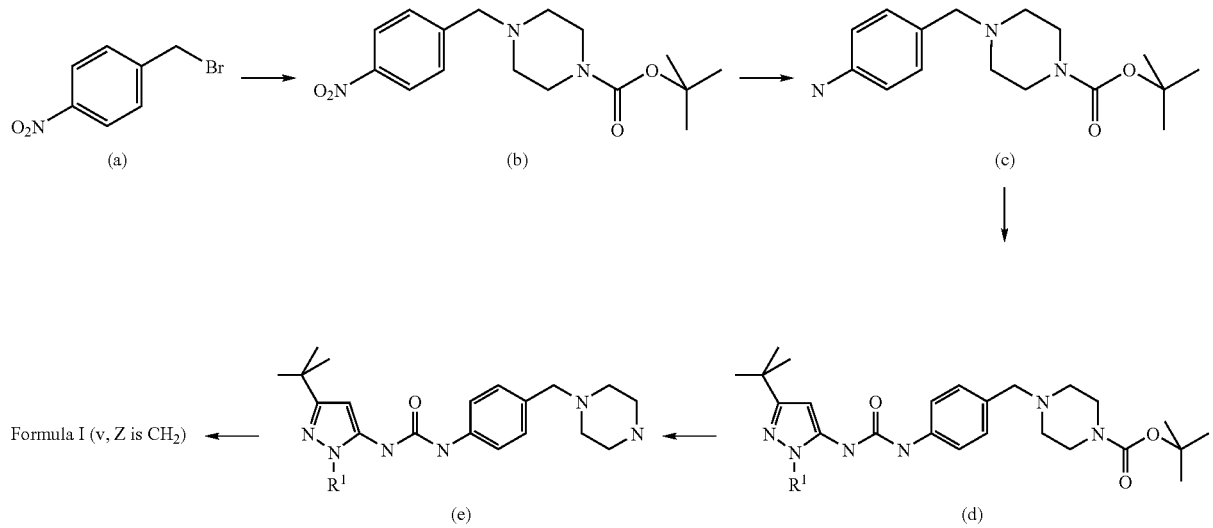

p-Nitrobenzylbromide (a) is reacted with the N-BOC protected piperazine in potassium carbonate in a polar solvent, preferably acetonitrile to provide the corresponding nitrobenzyl substituted piperazine (b). The nitro moiety is reduced with tin chloride in ethyl acetate to provide the corresponding amine (c). This amine is then reacted with an appropriate pyrazolyl-2,2,2-trichloroethyl carbamate to provide an N-BOC-piperazine substituted urea (d). After deprotection, the procedure provides the substituted piperazine (e). Finally, the substituted piperazine (e) is reacted with a substituted carboxylic acid under the standard coupling conditions for organic acids and organic amines in the presence of a dehydrating or coupling agent, such as carbonyl diimidazole; or with a substituted acid chloride in the presence of a base scavenger to give formula I(v). Furthermore, piperazine (e) may be acylated with e.g. acetic anhydride in the presence of a base to provide Formula I (v).

Scheme 7

Compounds of Formula I (v, Z is a bond) may be prepared as illustrated in the following Scheme where R$^1$ is defined as before:

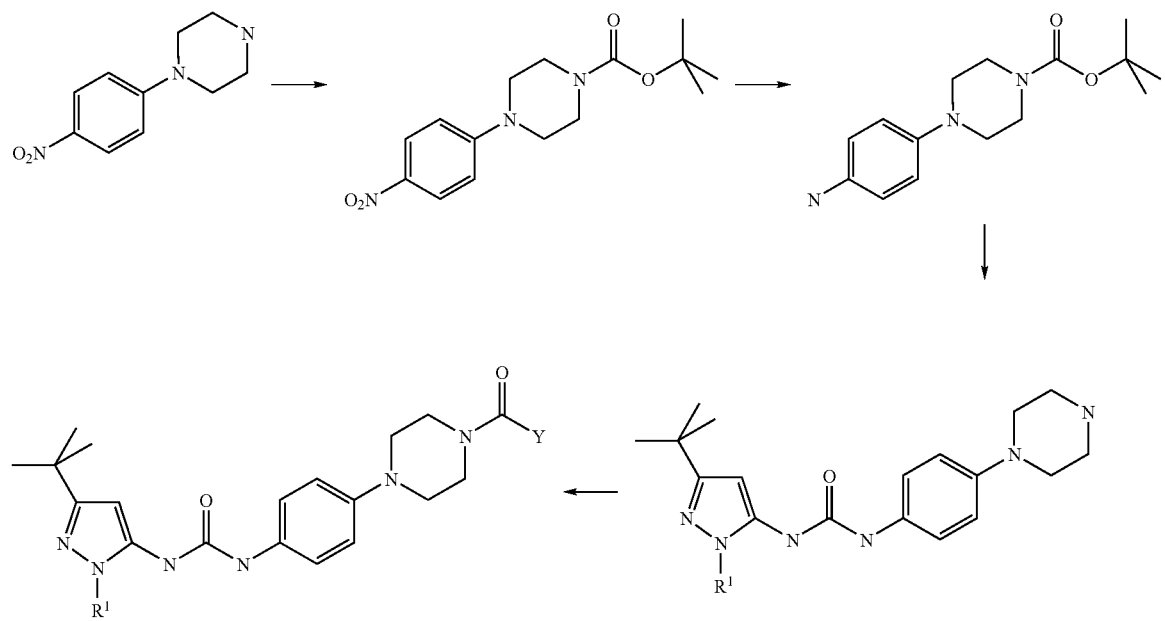

4-Nitro phenyl piperazine is protected as N-BOC derivative followed by reduction of the nitro group under hydrogenation conditions, typically catalyzed by Pd on carbon. This amine is then reacted with an appropriate pyrazolyl-2,2,2-trichloroethyl carbamate to provide an N-protected-piperazine substituted urea. After deprotection, the procedure provides the substituted piperazine. Finally, the substituted piperidine is reacted with a substituted carboxylic acid under the standard coupling conditions for organic acids and organic amines in the presence of a dehydrating or coupling agent, such as, a carbonyl diimidazole; or with a substituted acid chloride or sulfonyl chloride and a base scavenger to provide the final compounds The skilled artisan will also appreciate that not all of the substituents in the compounds of Formula I will tolerate certain reaction conditions employed to synthesize the compounds. These moieties may be introduced at a convenient point in the synthesis, or may be protected and then deprotected as necessary or desired. The skilled artisan will appreciate that the protecting groups may be removed at any convenient point in the synthesis of the compounds of the present invention. Methods for introducing and removing nitrogen and oxygen protecting groups are well known in the art; see, for example, Greene and Wuts, *Protective Groups in Organic Synthesis*, 3$^{rd}$ Ed., John Wiley and Sons, New York, Chapter 7 (1999). Furthermore, the skilled artisan will appreciate that in many circumstances, the order in which moieties are introduced is not critical. The particular order of steps required to produce the compounds of Formula I is dependent upon the particular compound being synthesized, the starting compound, and the relative lability of the substituted moieties.

The abbreviations, symbols and terms used in the examples and assays have the following meanings.

AcOH=acetic acid
DCC=dicyclohexylcarbodiimide
DEAD=Diethylazodicarboxylate
DIBAL=diisobutylaluminum hydride
DIEA=N,N-di-isopropylethylamine
DMSO=dimethylsulfoxide
DMF=N,N-dimethylformamide
hr=hour(s)
HCl=hydrochloric acid
HOB(t)=1-hydroxybenzotriazole
MnO$_2$=manganese dioxide
min=minute(s)
NaCl=sodium chloride
NaBH(OAc)$_3$=sodium triacetoxyborohydride
NaOH=sodium hydroxide
PS-DCC=carbodiimide bound to a solid phase
THF=tetrahydrofuran

PREPARATIONS

Preparation 1

4-(4-Nitro-phenoxy)-piperidinyl-1-carboxylic acid tert-butyl Ester

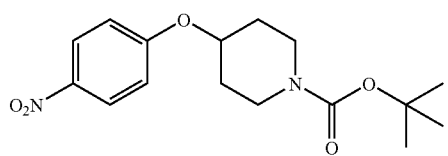

4-Hydroxy-1-piperidine-1-carboxylic acid tert-butyl ester (6.04 g, 30 mmol) is dissolved in 1-fluoro-4-nitrobenzene (7.83 g, 55.5 mmol). Then an aqueous potassium hydroxide solution (25% wt, 44 mL) is added, followed by addition of tetrabutylammonium bromide (1.26 g). The reaction mixture is stirred at 35° C. for 17 hours. The yellow solid is collected by filtration, washed with water (4×50 mL). A yellow powder is obtained (9.43 g, 97.5% yield).

Preparation 2

4-(4-Amino-phenoxy)-piperidinyl-1-carboxylic acid tert-butyl Ester

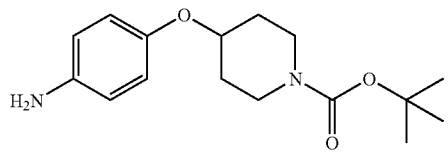

A mixture of 4-(4-nitro-phenoxy)-piperidine-1-carboxylic acid tert-butyl ester (3.15 g, 9.77 mmol) and 10% wt palladium on carbon (1.01 g) in anhydrous ethanol-methanol (1:1, 100 mL) is stirred vigorously under hydrogen gas at 22° C. for 2 hours. Then the palladium on carbon is removed by filtration. The filtrate is concentrated to give a white solid (2.35 g, 82.3% yield).

Preparation 3

(5-tert-Butyl-2-methyl-2H-pyrazol-3-yl)-carbamic acid 2,2,2-trichloro-ethyl Ester

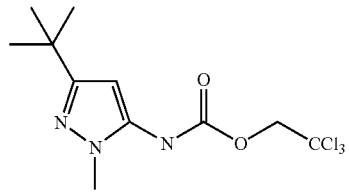

To an ice-cooled solution of 5-tert-butyl-2-methyl-2H-pyrazol-3-ylamine (0.50 g, 3.26 mmol) and pyridine (0.27 mL, 3.29 mmol) in THF (THF, 10 mL) is added 2,2,2-trichloroethyl chloroformate (0.44 mL, 3.29 mmol). The reaction mixture is stirred at 0° C. for 30 min and then warmed to room temperature for 2 hours. Then the reaction mixture is distributed between ethyl acetate (100 mL) and water (100 mL). The aqueous phase is extracted with ethyl acetate (50 mL). The combined organic phases are washed with saturated NaCl (2×50 mL) and dried over anhydrous magnesium sulfate. After removal of solvent, the residue is purified on a silica gel chromatography by washing with ethyl acetate to provide a white solid (0.83 g, 78%, ES+(m/z) 329.9 [M+H]).

Preparation 4

1-(5-tert-Butyl-2-methyl-2H-pyrazol-3-yl)-3-[4-(piperidin-4-yloxy)-phenyl]-urea

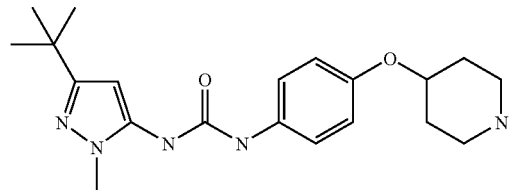

1-(5-tert-Butyl-2-methyl-2H-pyrazol-3-yl)-3-{4-[1-(tert-butoxy)carbonyl-piperidin-4-yloxy]phenyl}urea (Example 1. below, 2.25 g, 4.77 mmol) is suspended in a solution of trifluoroacetic acid in dichloromethane (25% v/v, 100 mL). The reaction mixture is stirred at 22° C. for 15 min. After removal of the solvent, the oily residue is neutralized with sodium hydroxide solution to pH 12 and extracted with dichloromethane (6×50 mL). The combined-organic phases are dried over anhydrous sodium sulfate and concentrated to yield a yellow solid (2.28 g, ES+(m/z) 372.1 [M+H]).

Preparation 5

(2,6-Dichlorobenzoyl)-(4-hydroxy-piperidin-1-yl)-methanone

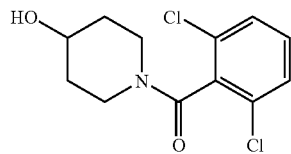

To an ice-cooled solution of 4-hydroxypiperidine (2.04 g, 20.2 mmol) and triethylamine (3.2 mL, 23.0 mmol) in dichloromethane (25 mL) is added 2,6-dichlorobenzoyl chloride (2.9 mL, 20.2 mmol). The reaction mixture is stirred at 0° C. for 2 hours and then washed with 1 N aqueous hydrochloric acid solution (50 mL), water (50 mL), and an aqueous saturated sodium bicarbonate solution (50 mL). The organic phase is dried over anhydrous sodium sulfate and concentrated to give a white solid (5.01 g, 90.5% yield, ES+(m/z) 276.1 [M+]).

Preparation 6

(4-Hydroxy-phenyl)-carbamic Acid Tert-butyl Ester

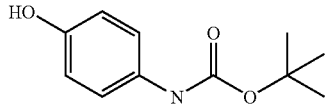

To a solution of 4-aminophenol (10.97 g, 100.5 mmol) and triethylamine (30 mL) in methanol (200 mL) is added di-tert-butyl dicarbonate (24.07 g, 110.3 mmol). The reaction mixture is stirred at 22° C. for 14 hours. After removal of solvent, the residue is distributed between ethyl acetate (250 mL) and 0.25 N aqueous hydrochloric acid solution (100 mL). The organic phase is isolated, washed with an aqueous saturated ammonium chloride solution (3×50 mL), and dried over anhydrous sodium sulfate. Removal of solvent affords a white solid (20.91 g, 100% yield, ES−(m/z) 208.1 [M−H]).

Preparation 7

{4-[1-(2,6-Dichloro-benzoyl)-piperidin-4-yloxy]-phenyl}-carbamic acid tert-butyl Ester

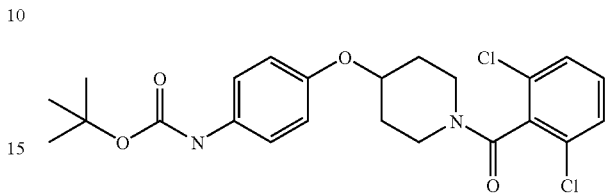

To an ice-cooled solution of (4-hydroxy-phenyl)-carbamic acid tert-butyl ester (422.8 mg, 2.02 mmol), (2,6-dichlorobenzoyl)-(4-hydroxy-piperidin-1-yl)-methanone (552.8 mg, 2.01 mmol), and triphenylphosphine (1.09 g, 4.16 mmol) in THF (20 mL) is added diethyl azodicarboxylate (1.0 mL, 2.20 mmol). The reaction mixture is stirred at 22° C. for 17 hours. After removal of solvent, the residue is purified on a silica gel chromatography with ethyl acetate-hexanes to provide a white solid (606.2 mg, 64.8% yield, ES+(m/z) 465.1 [M+H]).

Preparation 8

[4-(4-Amino-phenoxy)-piperidin-1-yl]-(2,6-dichlorophenyl)-methanone

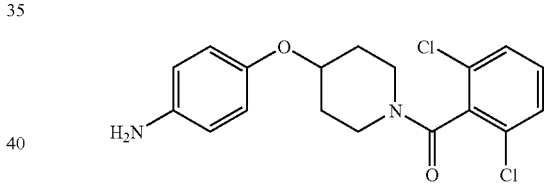

The above white solid, {4-[1-(2,6-dichloro-benzoyl)-piperidin-4-yloxy]-phenyl}-carbamic acid tert-butyl ester, is suspended in a solution of trifluoroacetic acid in dichloromethane (25% v/v, 20 mL). The reaction mixture is stirred at 22° C. for 15 min. After removal of the solvent, the oily residue is neutralized with 0.5 N aqueous sodium hydroxide solution (50 mL) and extracted with dichloromethane (5×50 mL). The combined organic phases are dried over anhydrous sodium sulfate and concentrated to yield a yellow solid (440.2 mg, 92.0% yield, ES+(m/z) 365.1 [M+H]).

The following preparations are prepared with methods analogous to methods in Preparations 5-8:

| No. | Intermediate name | Method(s) Analogous to: |
|---|---|---|
| Preparation 9 | [4-(4-Amino-phenoxy)-piperidin-1-yl]-(2-chlorophenyl)-methanone | Preparation 5-8 starting with 2-chlorobenzoyl chloride in Prep. 5 |
| Preparation 10 | [4-(4-Amino-phenoxy)-piperidin-1-yl]-(2,6-difluorophenyl)-methanone | Preparation 5-8 starting with 2,6-difluorobenzoyl chloride in Prep. 5 |

-continued

| No. | Intermediate name | Method(s) Analogous to: |
| --- | --- | --- |
| Preparation 11 | [4-(4-Amino-phenoxy)-piperidin-1-yl]-(cyclopropyl)-methanone | Preparation 5-8 starting with cyclopropylcarbonyl chloride in Prep. 5 |
| Preparation 12 | [4-(4-Amino-naphthyloxy)-piperidin-1-yl]-(2,6-dichlorophenyl)-methanone | Preparation 6-8 starting with 4-aminonaphthol in Prep. 6 |
| Preparation 13 | [4-(4-Amino-naphthyloxymethyl)-piperidin-1-yl]-(2,6-dichlorophenyl)-methanone | Preparation 5-8 starting with 4-piperidinylmethanol in Prep. 5 |
| Preparation 14 | {4-[2-(4-Amino-naphthyloxy)ethyl]-piperidin-1-yl}-(2,6-dichlorophenyl)-methanone | Preparation 5-8 starting with 4-piperidinylethanol in Prep. 5 |
| Preparation 15 | [4-(3-Amino-phenoxy)-piperidin-1-yl]-(2,6-dichlorophenyl)-methanone | Preparation 5-8 starting with 3-aminophenol in Prep. 6 |

Preparation 16

4-(5-Amino-2-methyl-phenoxy)-piperidin-1-yl)-(2-chloro-phenyl)-methanone

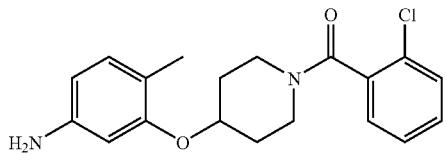

The intermediate is prepared by using Prep. 5-8 starting from 2-chlorobenzoyl chloride in Prep. 5 and 5-amino-o-cresol in Prep. 6. (ES+(m/z) 345.2 [M+H]).

Preparation 17

4-[2-(Dimethylamino)-ethoxy]-benzoic Acid Methyl Ester

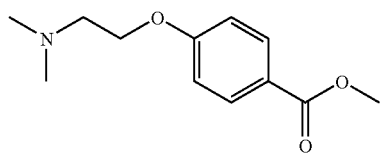

To an ice-water cooled solution of 2-dimethylamino-ethanol (305.0 mg, 3.0 mmol), 4-hydroxy-benzoic acid methyl ester (456.3 mg, 3.0 mmol), and triphenylphosphine (1.59 g, 6.0 mmol) in THF (4 mL) is added DEAD (40% solution in toluene, 2.75 mL, 6.0 mmol) dropwise. After stirred at 22° C. overnight, the reaction mixture is passed through a SGX column, washed with methanol, and eluded with 2M ammonia in methanol. Removal of the solvent gives a crude product, which is used in the next step without purification.

Preparation 18

4-[2-(Dimethylamino)-ethoxy]-benzoic Acid

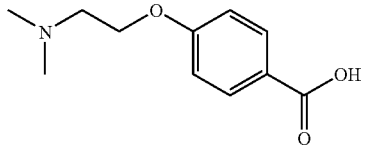

To a solution of 4-[2-(dimethylamino)-ethoxy]-benzoic acid methyl ester (3 mmol) in methanol (10 mL) is added a lithium hydroxide solution (2 M, 20 mL). The reaction mixture is stirred at 22° C. for 15 min. After removal of the solvent, the residue is re-dissolved in methanol, passed through a SCX column, washed with methanol, and eluded with 2M ammonia in methanol. After solvent is evaporated, a white solid is obtained (500 mg, 80% yield, ES−(m/z) 208.2 [M−H]).

Preparation 19

4-(3-tert-Butoxycarbonylamino-phenoxy)-piperidin-1-yl Carboxylic Acid Benzyl Ester

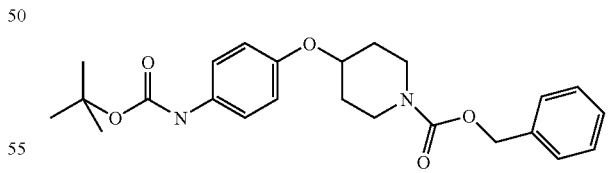

To an ice-cooled solution of 1,1-(azodicarbonyl) dipiperidine (18.08 g, 71.7 mmol) in anhydrous THF (200 mL) is added via syringe tributylphosphine (17.69 mL, 79.7 mmol) and allowed to stir for 2.5 hours. To this ice-cooled mixture is added a solution of (3-hydroxy-phenyl)-carbamic acid tert-butyl ester (10.0 g, 47.8 mmol) and 4-hydroxy-piperidine-1-carboxylic acid benzyl ester (7.23 mL, 47.8 mmol) in anhydrous THF (30 mL) causing a light yellow precipitate to form. The mixture is warmed to room temperature and stirred overnight. The mixture is filtered through a fritted funnel and washed solid with THF (3×15 mL). After removal of solvent, the residue is purified on a silica gel chromatography with ethyl acetate-hexanes to provide a clear oil (11.8 g, 57.9% yield, ES+(m/z) 427.2 [M+H]).

Preparation 20

4-(3-Amino-phenoxy)-piperidin-1-yl Carboxylic Acid Benzyl Ester

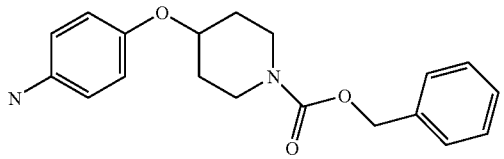

4-(3-tert-Butoxycarbonylamino-phenoxy)-piperidine-1-carboxylic acid benzyl ester (11.8 g, 27.6 mmol) is dissolved in a solution of trifluoroacetic acid in dichloromethane (25% v/v, 20 mL). The reaction mixture is stirred at 22° C. for 60 min. After removal of the solvent, the oily residue is dissolved in dichloromethane (250 mL) and neutralized with 0.2 N aqueous sodium hydroxide solution (250 mL) and extracted with dichloromethane (10×100 mL) followed by ethyl acetate (5×100 mL). The combined organic phases are dried over anhydrous sodium sulfate. After removal of solvent, the crude product is purified on silica gel chromatography with dichloromethane-methanol to give a light brown oil (4.84 g, 54%, ES+(m/z) 327.3 [M+H]).

Preparation 21

1-(5-tert-Butyl-2-methyl-2H-pyrazol-3-yl)-3-[3-(piperidin-4-yloxy)-phenyl]-urea

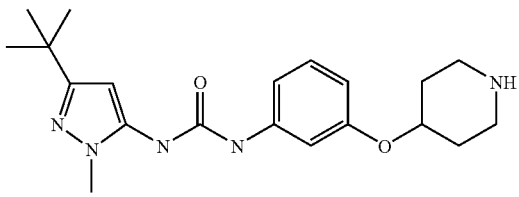

A mixture of 1-(5-tert-butyl-2-methyl-2H-pyrazol-3-yl)-3-{3-[1-(benzyloxy)-carbonyl-piperidin-4-yloxy]phenyl}urea. (Example 54. below, 6.62 g, 13.1 mmol) and 10% palladium on carbon (1 g) in ethanol (200 mL) is stirred at 22° C. under hydrogen gas for 2.5 hours. The catalyst is removed by filtration. The filtrate is concentrated to give brown oil, which solidifies upon standing at 22° C. over weekend. The residue is purified on a silica gel chromatography by eluting with methanol and dichloromethane. A peach color solid is obtained (3.51 g, 72% yield, ES+(m/z) 372.3 [M+H]).

Preparation 22

3-Nitro-5-trifluoromethyl-phenol

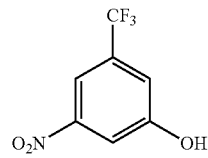

To a solution of 3-methyl-5-trifluoromethyl-nitrobenzene (3.80 g, 17.2 mmol) in dichloromethane (10 mL) at −78° C. is added a solution of boron tribromide (1M in DCM, 100 mL, 100 mmol). The reaction mixture is allowed to warm up to 22° C. and stirred overnight. Next, the reaction is quenched with a saturated sodium bicarbonate solution and extracted with ethyl acetate (4×100 mL). The combined organic phases are dried over sodium sulfate and concentrated. The residue is purified on silica gel with hexanes-ethyl acetate to yield a yellow solid (2.6 g, 73% yield).

Preparation 23

1-(5-tert-Butyl-2-methyl-2H-pyrazol-3-yl)-3-[3-(piperidin-4-yloxy)-5-trifluoromethyl-phenyl]-urea

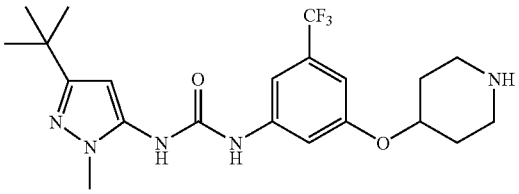

The intermediate is synthesized by using the method of Preparation 7 and 2, Example 1, and Preparation 4 from intermediate 22. (ES+(m/z) 440.2 [M+H]).

Preparation 24

[1-(4-Methanesulfonyl-benzoyl)-piperidin-4-yl]-carbamic Acid Tert-butyl Ester

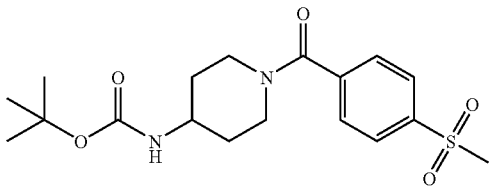

To an ice-cooled slurry of 4-N-BOC-amino-piperidine (400.8 mg, 2.0 mmol), 1-hydroxybenzotriazole (HOBt, 342.3 mg, 2.53 mmol), and p-(methylsulfonyl)-benzoic acid (445.9 mg, 2.23 mmol) in dichloromethane (6 mL) is added 1,3-dicyclohexylcarbodiimide (DCC, 496.7 mg, 2.40 mmol). The reaction mixture is stirred at 22° C. for 23 hours. The crude product is purified on a silica gel chromatography with ethyl acetate-hexanes to provide a white solid (692.9 mg, 90.6% yield, ES+(m/z) 383.1 [M+H]).

Preparation 25

(4-Amino-piperidin-1-yl)-(4-methanesulfonyl-phenyl)-methanone

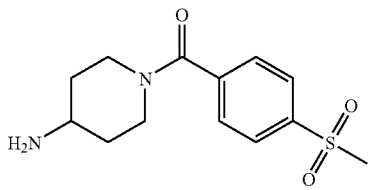

The above white solid is suspended in a solution of trifluoroacetic acid in dichloromethane (25% v/v, 20 mL). The reaction mixture is stirred at 22° C. for 15 min. After removal of the solvent, the oily residue is neutralized with 0.5 N aqueous sodium hydroxide solution and extracted with dichloromethane (5×50 mL). The combined organic phases are dried over anhydrous sodium sulfate and concentrated to yield a white solid (308.1 g, 60.2% yield, ES+(m/z) 283.2 [M+H]).

Preparation 26

[4-(3-Amino-phenyl)-piperidin-1-yl]-(2,6-dichlorophenyl)-methanone

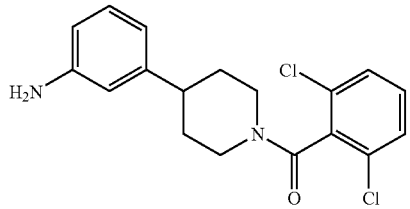

To an ice-cooled solution of 4-(3-aminophenyl)-piperidine hydrochloride (250.2 mg, 1.0 mmol) and triethylamine (1 mL) in dichloromethane (6 mL) is added 2,6-dichlorobenzoic chloride (0.15 mL, 1.0 mmol). The reaction mixture is stirred at 0° C. for 6 hours. After removal of solvent, the residue is purified on a silica gel chromatography with ethyl acetate-hexanes to provide a white solid (163.9 mg, 46.9% yield, ES+(m/z) 349.1 [M+H]).

Preparation 27

4-[3-(5-tert-Butyl-2-methyl-2H-pyrazol-3-yl)-ureido]-benzoic Acid Ethyl Ester

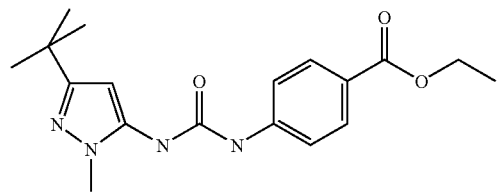

To 1.0 g (6.53 mmol) of 5-tert-butyl-2-methyl-2H-pyrazol-3-ylamine in 10 mL of $CH_2Cl_2$ is added 1.37 g (7.17 mmol) of 4-isocyanate-benzoic acid ethyl ester, and the mixture is stirred at 23° C. for 3 hours. The white solid is filtered and triturated with methylene chloride and then with diethyl ether. The solids are air-dried 1 hour to obtain the title product (2.07 g, 6.01 mmol, 92% yield, ES+(m/z) 345 [M+H]).

Preparation 28

1-(5-tert-Butyl-2-methyl-2H-pyrazol-3-yl)-3-(4-hydroxymethyl-phenyl)urea

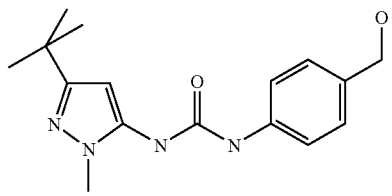

To a dry flask is added 872 mg (2.5 mmol) of 4-[3-(5-tert-butyl-2-methyl-2H-pyrazol-3-yl)-ureido]-benzoic acid ethyl ester in 30 mL dry methylene chloride and cooled to 0° C. Next, 10.12 mL of 1M DIBAL in hexanes (4 eq., 10.12 mmol) is added and the reaction is allowed to reach room temperature. The mixture is then stirred for 1 hour, and 60 mL of ethyl acetate and 100 mL of sodium tartrate saturated aqueous solution are added, and the mixture is stirred for another 30 min. Then the organic layer is separated and washed with water and dried over magnesium sulfate, filtered, and evaporated to a white solid weighing 720 mg (2.4 mmoles, 95%, ES+(m/z) 303 [M+H]).

Preparation 29

1-(5-tert-Butyl-2-methyl-2H-pyrazol-3-yl)-3-(4-formyl-phenyl)-urea

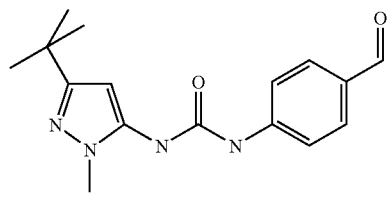

To a suspension of 518 mg (1.72 mmol) of 1-(5-tert-butyl-2-methyl-2H-pyrazol-3-yl)-3-(4-hydroxymethyl-phenyl)-urea in methylene chloride (25 mL) is added 2.7 g of $MnO_2$. The mixture is stirred at room temperature for 3 hours. Then the mixture is filtered over Celite® and evaporated to obtain 353 mg (1.2 mmol, 68%) of the title compound as a white solid. (ES+(m/z) 301 [M+H]).

Preparation 30

1-(5-tert-Butyl-2-methyl-2H-pyrazol-3-yl)-3-(4-piperazin-1-ylmethyl-phenyl)-urea Dihydrochloride

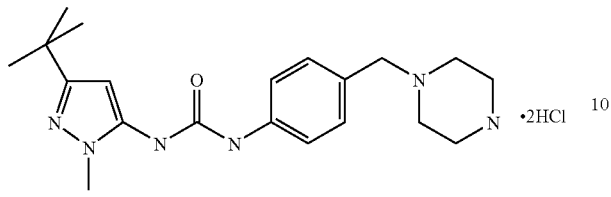

To a suspension of 353 mg (1.18 mmol) of 1-(5-tert-butyl-2-methyl-2H-pyrazol-3-yl)-3-(4-formyl-phenyl)-urea in 1,2-dichloroethane (20 mL) is added piperazine-1-carboxylic acid tert-butyl ester (219 mg, 1.18 mmol). Next, NaBH(OAc)$_3$ is added (350 mg, 1.65 mmol). The reaction mixture is stirred at room temperature overnight. Then the mixture is diluted with methylene chloride and 10 mL of 1 N NaOH is added. The organic layer is separated and dried over sodium sulfate, filtered and evaporated at reduced pressure to afford 485 mg of the N-BOC protected compound as a colorless oil. ES+(m/z)=471 [M+H]. Then 10 mL of a 4M solution of HCl in dioxane is added and the mixture is stirred for 2 hours at room temperature. The solvents are evaporated at reduced pressure to afford the title compound 457 mg (1.03 mmol, 87%) as a white solid. (ES+(m/z) 371 [M+H].

Preparation 31

3-[3-(5-tert-Butyl-2-methyl-2H-pyrazol-3-yl)-ureido]-benzoic Acid Ethyl Ester

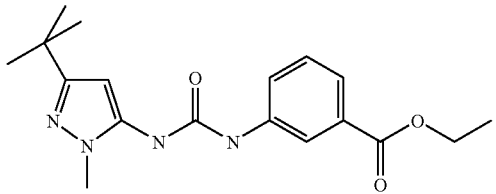

Using the same procedure as in Preparation 27 and starting from 3-Isocyanato-benzoic acid ethyl ester the title compound is synthesized. (ES+(m/z) 345 [M+H].

Preparation 32

1-(5-tert-Butyl-2-methyl-2H-pyrazol-3-yl)-3-(3-hydroxymethyl-phenyl)-urea

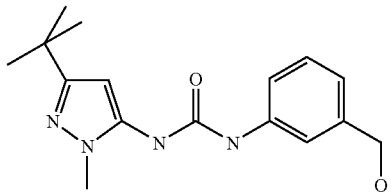

Using the same procedure as in Preparation 28, starting from 3-[3-(5-tert-Butyl-2-methyl-2H-pyrazol-3-yl)-ureido]-benzoic acid ethyl ester the title compound is synthesized. (ES+(m/z) 303 [M+H].

Preparation 33

1-(5-tert-Butyl-2-methyl-2H-pyrazol-3-yl)-3-(3-formyl-phenyl)-urea

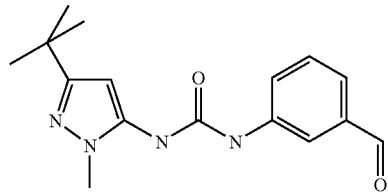

Using the same procedure as in Preparation 29, starting from 1-(5-tert-Butyl-2-methyl-2H-pyrazol-3-yl)-3-(3-hydroxymethyl-phenyl)-urea the title compound is synthesized. (ES+(m/z) 301 [M+H].

Preparation 34

1-(5-tert-Butyl-2-methyl-2H-pyrazol-3-yl)-3-(3-piperazin-1-ylmethyl-phenyl)-urea Dihydrochloride

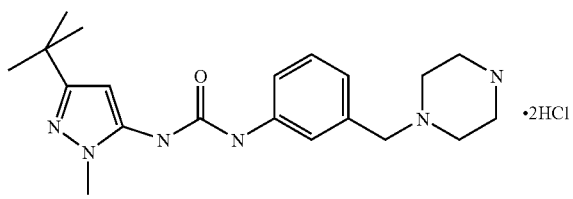

Using the same procedure as in Preparation 30, starting from 1-(5-tert-Butyl-2-methyl-2H-pyrazol-3-yl)-3-(3-formyl-phenyl)-urea the title compound is synthesized. (ES+(m/z) 371 [M+].

Preparation 35

4-[3-(5-tert-Butyl-2-methyl-2H-pyrazol-3-yl)-ureido]benzoic Acid

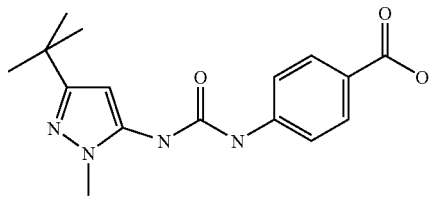

To a suspension of 4-[3-(5-tert-butyl-2-methyl-2H-pyrazol-3-yl)-ureido]benzoic acid ethyl ester (0.24 g, 0.71 mmol) in ethanol (4 mL) is added 1 N aq. NaOH solution (2 mL) and the mixture is heated at 80° C. for 2 hours. Then, 1 N HCl is added until pH 6 and the mixture is diluted with ethyl acetate. The organic phase is washed once with aqueous sodium chloride solution and dried over magnesium sulfate, filtered and evaporated under reduced pressure to give 0.19 g (0.59 mmol), 83% as white solid. ES+(m/z) 317 [M+H].

Preparation 36

5-tert-Butyl-2-isopropyl-2H-pyrazol-3-ylamine

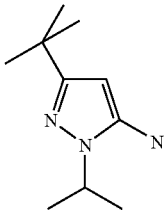

To a solution of 4,4-dimethyl-3-oxo-pentanenitrile (1 g, 7.99 mmol) and isopropyl hydrazine hydrochloride (873 mg, 7.99 mmol) in toluene (40 mL) is added DIEA (1.39 mL, 7.99 mmol). The reaction mixture is stirred at 110° C. in a sealed tube overnight. After removal of solvent, the residue is purified on a silica gel chromatography with ethyl acetate-hexanes to give a white solid (1.14 g, 79% yield, ES+(m/z) 182 [M+H]).

The following preparations are prepared with a method analogous to Preparation 36.

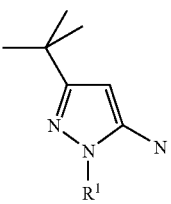

| No. | Intermediate Name | $R^1$ | ES+ m/z [M + H] | Synthetic Method(s) Analogous to: |
|---|---|---|---|---|
| Prep 37 | 2,5-Di-tert-butyl-2H-pyrazol-3-ylamine | tert-Butyl | 196 | Prep 36 with tert-butyl hydrazine hydrochloride |
| Prep 38 | 5-tert-Butyl-2-ethyl-2H-pyrazol-3-ylamine | Ethyl | 168 | Prep 36 with ethyl hydrazine oxalate |

The following preparations are prepared with a method analogous to Preparation 3:

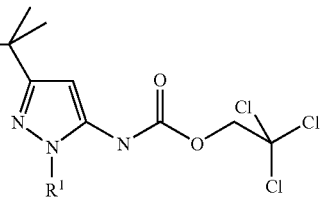

| No. | Intermediate Name | $R^1$ | ES+ m/z [M + H] |
|---|---|---|---|
| Prep 40 | (2,5-Di-tert-butyl-2H-pyrazol-3-yl)-carbamic acid 2,2,2-trichloro-ethyl ester | tert-butyl | 371 |
| Prep 41 | (5-tert-Butyl-2-ethyl-2H-pyrazol-3-yl)-carbamic acid 2,2,2-trichloro-ethyl ester | Ethyl | 343 |

-continued

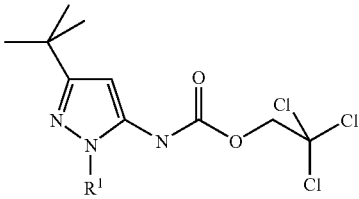

| No. | Intermediate Name | $R^1$ | ES+ m/z [M + H] |
|---|---|---|---|
| Prep 42 | (5-tert-Butyl-2-isopropyl-2H-pyrazol-3-yl)-carbamic acid 2,2,2-trichloro-ethyl ester | Isopropyl | 357 |
| Prep 43 | (5-tert-Butyl-2-p-tolyl-2H-pyrazol-3-yl)-carbamic acid 2,2,2-trichloro-ethyl ester | Tolyl | 406 |

Preparation 44

4-(4-Nitro-benzyl)-piperazinyl-1-carboxylic acid tert-butyl ester

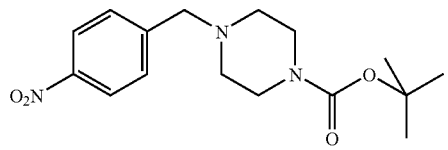

A mixture of 1-Bromomethyl-4-nitro-benzene (2 g, 9.26 mmol), N-BOC piperazine (1.72 g, 9.26 mmol) and potassium carbonate (2.8 g, 20.37 mmol) in acetonitrile (25 mL) is stirred at 80° C. overnight. Then, the potassium carbonate is removed by filtration. The filtrate is concentrated to give a white solid (2.63 g, 89% yield, ES+(m/z) 322 [M+H]).

Preparation 45

4-(4-Amino-benzyl)-piperazin-1-yl Carboxylic Acid Tert-butyl Ester

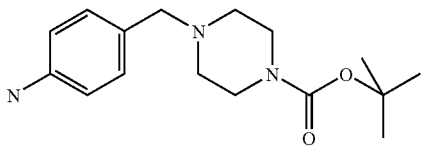

4-(4-Nitro-benzyl)-piperazin-1-yl carboxylic acid tert-butyl ester (769 mg, 2.4 mmol) and tin chloride dihydrate (2.70 g, 12 mmol) are suspended in ethyl acetate (20 mL) and stirred at room temperature overnight. Then, saturated aqueous solution of sodium bicarbonate (20 mL) is added and vigorously stirred for 1 hour. Solids are removed by filtration and the organic layer of the filtrate is separated and washed with water (20 mL). The organic phase is dried over anhydrous magnesium sulfate and concentrated to give a white solid (620 mg, 89% yield, ES+(m/z) 293 [M+H]).

The following preparations are prepared using the method of Example 1 (see below):

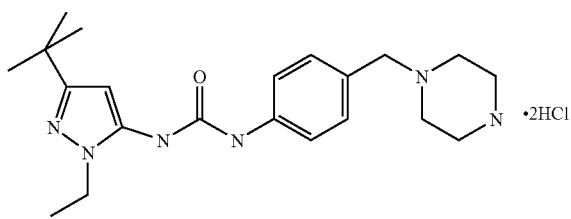

| No. | Intermediate Name | $R^1$ | ES+ m/z [M + H] | Synthetic Method(s) Analogous to: |
|---|---|---|---|---|
| Prep 46 | 4-{4-[3-(5-tert-Butyl-2-isopropyl-2H-pyrazol-3-yl)-ureido]-benzyl}-piperazin-1-yl carboxylic acid tert-butyl ester | Iso-propyl | 499 | Ex. 1 using cpd from Prep 42 |
| Prep 47 | 4-{4-[3-(5-tert-Butyl-2-ethyl-2H-pyrazol-3-yl)-ureido]-benzyl}-piperazinyl-1-carboxylic acid tert-butyl ester | Ethyl | 485 | Ex. 1 using cpd from Prep 41 |

Preparation 48

1-(5-tert-Butyl-2-ethyl-2H-pyrazol-3-yl)-3-(4-piperazin-1-ylmethyl-phenyl)-urea Dihydrochloride

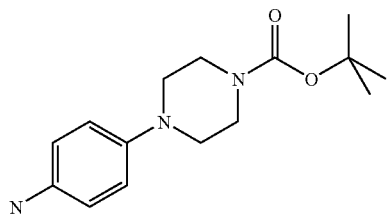

4-{4-[3-(5-tert-Butyl 2-ethyl-2H-pyrazol-3-yl)-ureido]-benzyl}-piperazine-1-carboxylic acid tert-butyl ester (105 mg, 0.216 mmol) is dissolved in dichloromethane (3 mL) and a 4M solution of HCl in 1,4-dioxane (0.86 mL, 3.5 mmol) is added and the mixture stirred at room temperature for 2 hours. After removal of solvent, the residue is triturated with diethyl ether and air-dried to obtain the title compound (99 mg, 99% yield, ES+(m/z) 385 [M+H]).

The following preparation is prepared with method analogous to Preparation 48.

| No. | Intermediate Name | $R^1$ | ES + m/z [M + H] | Synthetic Method(s) Analogous to: |
|---|---|---|---|---|
| Prep 49 | 1-(5-tert-Butyl-2-isopropyl-2H-pyrazol-3-yl)-3-(4-piperazin-1ylmethyl-phenyl)-urea | Isopropyl | 371 | Preparation 48 |

Preparation 50

4-(4-Nitro-phenyl)-piperazin-1-yl carboxylic acid tert-butyl ester

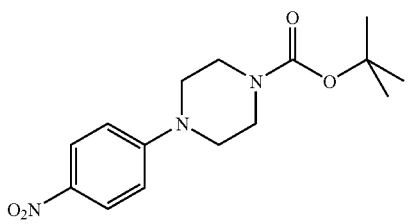

1-(4-Nitro-phenyl)-piperazine (2 g, 9.65 mmol) is dissolved in dichloromethane (50 mL) and (BOC)$_2$O is added (2.10 g, 9.65 mmol). The mixture is stirred at room temperature overnight. Solvent removal affords a yellow solid (2.96 g, 100% yield, ES+(m/z) 308 [M+H]).

Preparation 51

4-(4-Amino-phenyl)-piperazin-1-yl Carboxylic Acid Tert-butyl Ester

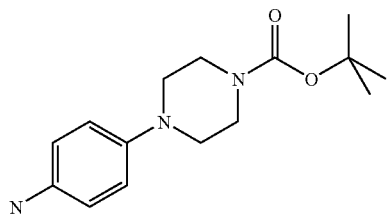

Using the same procedure as in Preparation 45 the title compound is synthesized. ES+(m/z) 278 [M+H]).

Preparation 52

4-{4-[3-(5-tert-Butyl-2-methyl-2H-pyrazol-3-yl)-ureido]-phenyl}-piperazin-1-yl Carboxylic Acid Tert-butyl Ester

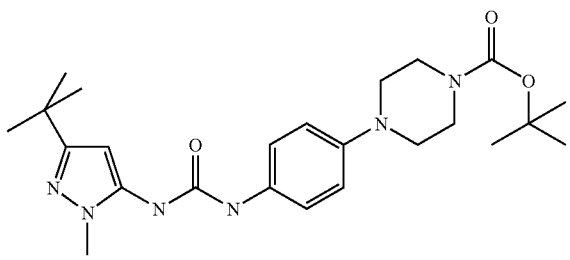

Using the method of Example 1 (see below) the title compound is synthesized ES+(m/z) 457 [M+H]).

Preparation 53

4-{4-[3-(5-tert-Butyl-2-p-tolyl-2H-pyrazol-3-yl)-ureido]-phenyl}-piperazin-1-yl Carboxylic Acid Tert-butyl Ester

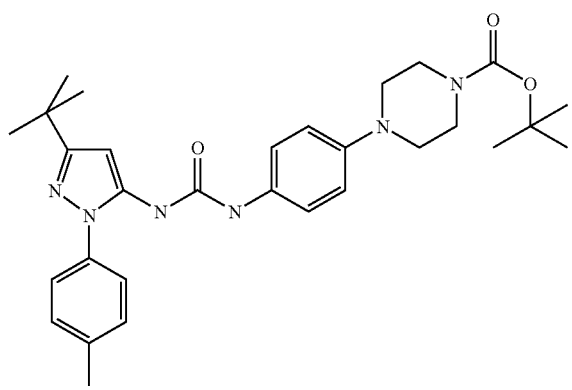

4-(4-Amino-phenyl)-piperazin-1-yl carboxylic acid tert-butyl ester (0.51 g, 1.8 mmol) is dissolved in 20 mL of $CH_3CN$ and $K_2CO_3$ (0.28 g, 2.02 mmol) is added, followed by addition of (5-tert-Butyl-2-p-tolyl-2H-pyrazol-3-yl)-carbamic acid 2,2,2-trichloro-ethyl ester (0.74 g, 2.02 mmol). Solution is stirred overnight at room temperature under $N_2$ atmosphere. Reaction mixture is diluted by addition of $CH_2Cl_2$ (100 mL) and washed with saturated aqueous solution of sodium chloride and water. The organic layer is dried over $MgSO_4$, and the solvent is evaporated under reduced pressure. Resultant crude is purified by ISCO using a mixture $CH_2Cl_2$/MeOH as eluent. (0.72 g, 75% yield, ES+(m/z) 533 [M+H]).

The following preparations are prepared with method analogous to Preparation 48:

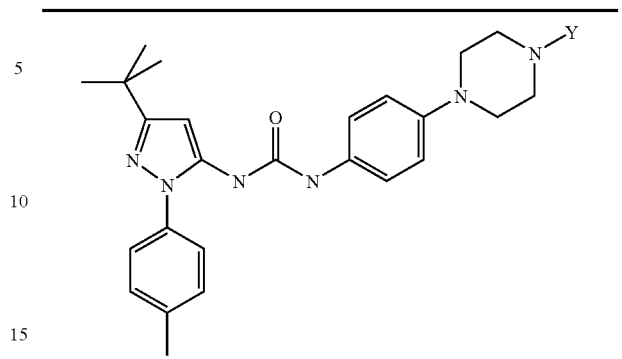

| No. | Intermediate Name | R¹ | ES+ m/z [M + H] | Synthetic Method(s) Analogous to: |
|---|---|---|---|---|
| Prep 54 | 1-(5-tert-Butyl-2-methyl-2H-pyrazol-3-yl)-3-(4-piperazin-1-yl-phenyl)-urea dihydrochloride | Methyl | 357 | Prep 48 |
| Prep 55 | 1-(5-tert-Butyl-2-p-tolyl-2H-pyrazol-3-yl)-3-(4-piperazin-1-yl-phenyl)-urea dihydrochloride | Tolyl | 433 | Prep 48 |

Using essentially the methodology of Example 97 (see below) but with $Et_3N$ and $CH_2Cl_2$ the following examples are prepared:

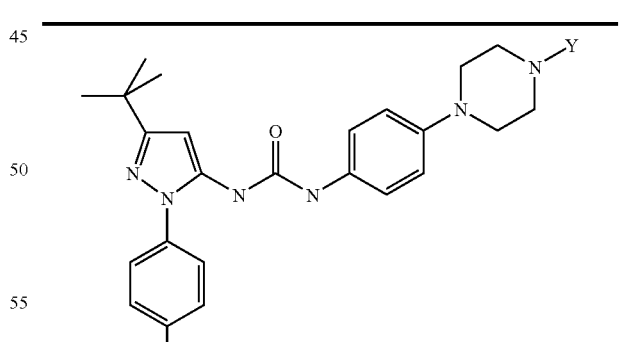

| No. | Name | Y | ES+ m/z [M + H] | Synthetic Method(s) Analogous to: |
|---|---|---|---|---|
| Prep 56 | 1-(5-tert-Butyl-2-p-tolyl-2H-pyrazol-3-yl)-3-{4-[4-(2,6-difluoro-benzoyl)-piperazin-1-yl]-phenyl}-urea | 2,6-difluoro-benzoyl | 573 | Ex. 97 with 2,6-di-fluorobenzoyl chloride |
| Prep 57 | 1-(5-tert-Butyl-2-p-tolyl-2H-pyrazol-3-yl)-3-{4-[4-(2,6-dichloro-benzoyl)-piperazin-1-yl]-phenyl}-urea | 2,6-dichloro-benzoyl | 606 | Ex. 97 with 2,6-di-chlorobenzoyl chloride |
| Prep 58 | 1-(5-tert-Butyl-2-p-tolyl-2H-pyrazol-3-yl)-3-[4-(4-cyclopropyl-piperazin-1-yl)-phenyl]-urea | Cyclo-propyl-carbonyl | 501 | Ex. 97 with cyclopropyl-carbonyl-chloride |
| Prep 59 | 1-[4-(4-tert-Butyl-piperazin-1-yl)-phenyl]-3-(5-tert-butyl-2-p-tolyl-2H-pyrazol-3-yl)-urea | tert-Butyl carbonyl | 517 | Ex. 97 with pivaloyl chloride |

Using essentially the methodology of Example 128 (see below) (reaction of 1-(5-tert-Butyl-2-p-tolyl-2H-pyrazol-3-yl)-3-(4-piperazin-1-yl-phenyl)-urea with the corresponding carboxylic acid) the following compound is prepared.

| No. | Name | Y | ES+ m/z [M + H] | Synthetic Method(s) Analogous to: |
|---|---|---|---|---|
| Prep 60 | 1-(5-tert-Butyl-2-p-tolyl-2H-pyrazol-3-yl)-3-[4-(4-isobutyryl-piperazin-1-yl)-phenyl]-urea | Isobutyric acid | 503 | Example 128 |

Preparation 61

1-Bromomethyl-2-fluoro-4-nitro-benzene

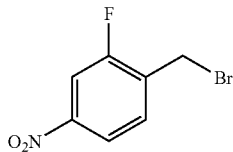

To a solution of 2-Fluoro-1-methyl-4-nitro-benzene (1 g, 6.45 mmol) and sodium bromate (2.92 g, 19.33 mmol) in an EtOAc:water (12 mL:9 mL) mixture, is added dropwise via addition funnel a 3.85M solution of sodium bisulfite 5.20 mL, 19.33 mmol). The mixture is vigorously stirred for six days and then sodium bisulfite (10 mL) is added and organic layer separated and washed with aqueous saturated solution of sodium bicarbonate. The organic phase is dried with magnesium sulfate, filtered and evaporated at reduced pressure to afford a mixture of title compound and starting 2-fluoro-1-methyl-4-nitro-benzene in a 5:1 ratio (1H-NMR) which is used in the next step without further purification. ES+(m/z) 235 [M+H]).

Preparation 62

4-Bromomethyl-2-fluoro-1-nitro-benzene

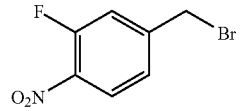

Using the same procedure as in Preparation 56, but starting from 2-fluoro-4-methyl-1-nitro-benzene, the title compound is synthesized. ES+(m/z) 235 [M+H]).

Using the same procedure as in Preparation 44, followed by Preparation 48, the following compounds are prepared:

| No. | Intermediate Name | ES + m/z [M + H] | Synthetic Method(s) Analogous to: |
|---|---|---|---|
| Prep 63 | 1-(3-Fluoro-4-nitro-benzyl)-piperazine dihydrochloride | 240 | Prep 44, and then Prep 48 |
| Prep 64 | 1-(2-Fluoro-4-nitro-benzyl)-piperazine dihydrochloride | 240 | Prep 44, and then Prep 48 |

Using essentially the methodology of Example 97 (see below) the following compounds are prepared:

| No. | Intermediate Name | ES + m/z [M + H] | Synthetic Method(s) Analogous to: |
|---|---|---|---|
| Prep 65 | (2,6-Difluoro-phenyl)-[4-(2-fluoro-4-nitro-benzyl)-piperazin-1-yl]-methanone | 380 | Ex. 97 with 2,6-difluorobenzoyl chloride |
| Prep 66 | (2,4-Difluoro-phenyl)-[4-(2-fluoro-4-nitro-benzyl)-piperazin-1-yl]-methanone | 380 | Ex. 97 with 2,4-difluorobenzoyl chloride |
| Prep 67 | (2,6-Difluoro-phenyl)-[4-(3-fluoro-4-nitro-benzyl)-piperazin-1-yl]-methanone | 380 | Ex. 97 with 2,6-difluorobenzoyl chloride |
| Prep 68 | (2,6-Dichloro-phenyl)-[4-(3-fluoro-4-nitro-benzyl)-piperazin-1-yl]-methanone | 413 | Ex. 97 with 2,6-dichlorobenzoyl chloride |
| Prep 69 | (2,4-Difluoro-phenyl)-[4-(3-fluoro-4-nitro-benzyl)-piperazin-1-yl]-methanone | 380 | Ex. 97 with 2,4-difluorobenzoyl chloride |

Using the same procedure as in Preparation 45, the following compounds are synthesized:

| No. | Intermediate Name | ES + m/z [M + H] | Synthetic Method(s) Analogous to: |
|---|---|---|---|
| Prep 70 | [4-(4-Amino-2-fluoro-benzyl)-piperazin-1-yl]-(2,6-difluoro-phenyl)-methanone | 350 | Preparation 45 |
| Prep 71 | [4-(4-Amino-2-fluoro-benzyl)-piperazin-1-yl]-(2,4-difluoro-phenyl)-methanone | 350 | Preparation 45 |
| Prep 72 | [4-(4-Amino-3-fluoro-benzyl)-piperazin-1-yl]-(2,6-difluoro-phenyl)-methanone | 350 | Preparation 45 |
| Prep 73 | [4-(4-Amino-3-fluoro-benzyl)-piperazin-1-yl]-(2,6-dichloro-phenyl)-methanone | 383 | Preparation 45 |
| Prep 74 | [4-(4-Amino-3-fluoro-benzyl)-piperazin-1-yl]-(2,4-difluoro-phenyl)-methanone | 350 | Preparation 45 |

EXAMPLES

Example 1

1-(5-tert-Butyl-2-methyl-2H-pyrazol-3-yl)-3-{4-[1-(tert-butoxy)carbonyl-piperidin-4-yloxy]phenyl}urea

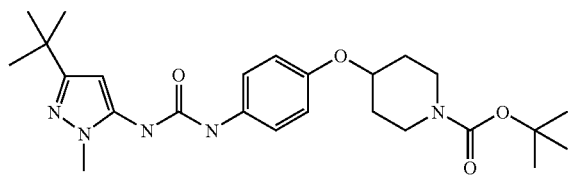

Nitrogen gas is bubbled through a solution of (5-tert-butyl-2-methyl-2H-pyrazol-3-yl)-carbamic acid 2,2,2-trichloro-ethyl ester (1.65 g, 5.01 mmol) and 4-(4-amino-phenoxy)-piperidine-1-carboxylic acid tert-butyl ester (1.47 g, 5.02 mmol) in DMSO (20 mL) for 2 min. Next, N,N-diisopropylethylamine (2 mL, 11.48 mmol) is added. The reaction mixture is stirred at 60° C. for 6 hours. Then, the reaction mixture is distributed between water (150 mL) and dichloromethane (100 mL). The aqueous layer is isolated and extracted with dichloromethane (2×100 mL). The combined organic phases are washed with water (100 mL) and aqueous sodium chloride (100 mL), and dried over anhydrous sodium sulfate. After removal of solvent, the crude product is purified on a silica gel chromatography with ethyl acetate-hexanes (25%) to give a white solid (2.28 g, 97%, ES−(m/z) 470.1 [M−H]).

Example 2

1-(5-tert-Butyl-2-methyl-2H-pyrazol-3-yl)-3-{4-[1-(benzoyl)-piperidin-4-yloxy]phenyl}urea

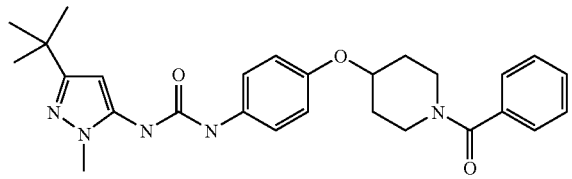

To an ice-cooled solution of 1-(5-tert-butyl-2-methyl-2H-pyrazol-3-yl)-3-[4-(piperidin-4-yloxy)-phenyl]-urea (82.2 mg, 0.22 mmol), 1-hydroxybenzotriazole (HOBt, 50.1 mg, 0.37 mmol), and benzoic acid (38.8 mg, 0.32 mmol) in dichloromethane-THF (1:1, 2 mL) is added DCC (52.0 mg, 0.25 mmol). The reaction mixture is stirred at 22° C. for 19 hours. The crude product is purified on a silica gel chromatography with ethyl acetate-hexanes to provide a white solid (97.7 mg, 93.4% yield, ES+(m/z) 476.1 [M+H]).

Example 3

1-(5-tert-Butyl-2-methyl-2H-pyrazol-3-yl)-3-{4-[1-(2,6-dichlorobenzoyl)-piperidin-4-yloxy]phenyl}urea

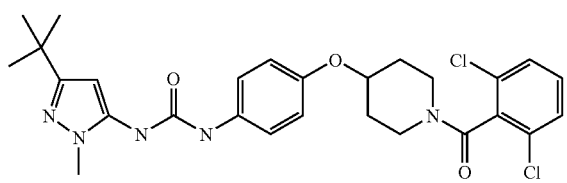

Nitrogen gas is bubbled through a solution of [4-(4-amino-phenoxy)-piperidin-1-yl]-(2,6-dichlorophenyl)-methanone (47 mg, 0.12 mmol) and (5-tert-butyl-2-methyl-2H-pyrazol-3-yl)-carbamic acid 2,2,2-trichloro-ethyl ester (42 mg, 0.12 mmol) in DMSO (1.5 mL) for 5 min. Next, N,N-diisopropylethylamine (40 μL, 0.24 mmol) is added. The reaction mixture is stirred at 60° C. for 6 hours. Then, DMSO is removed by passing the reaction mixture through an SCX column. The crude product is obtained by eluting the SCX column with 2M ammonia in methanol and purifying the residue on silica gel with ethyl acetate-hexanes (25%) to give a white solid (ES+ (m/z) 544.2 [M+H]).

Using the method of Example 2 or 3 gives the following compounds, isolated as the free base, wherein the urea nitrogen is always connected to a carbon atom in W':

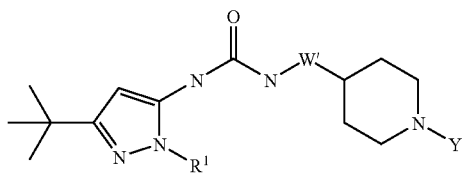

| Ex. No. | Name | $R^1$ | W' | Y | ES+ m/z [M + H] | Synthetic Method(s) Analogous to: |
|---|---|---|---|---|---|---|
| 4 | 1-(5-tert-Butyl-2-methyl-2H-pyrazol-3-yl)-3-{4-[1-(cyclopropyl)carbonyl-piperidin-4-yloxy]phenyl}urea | Me | 1,4-phenyl-O— | Cyclopropyl carbonyl | 440.2 | Ex 2 using YOH |

-continued

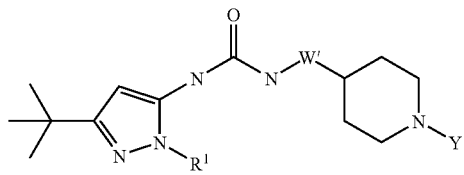

| Ex. No. | Name | R¹ | W' | Y | ES+ m/z [M + H] | Synthetic Method(s) Analogous to: |
|---|---|---|---|---|---|---|
| 5 | 1-(5-tert-Butyl-2-methyl-2H-pyrazol-3-yl)-3-{4-[1-(isopropyl)carbonyl-piperidin-4-yloxy]phenyl}urea | Me | 1,4-phenyl-O— | Isopropyl carbonyl | 442.1 | Ex 2 using YOH |
| 6 | 1-(5-tert-Butyl-2-methyl-2H-pyrazol-3-yl)-3-{4-[1-(tert-butyl)carbonyl-piperidin-4-yloxy]phenyl}urea | Me | 1,4-phenyl-O— | tert-Butyl carbonyl | 456.3 | Ex 2 using YOH |
| 7 | 1-(5-tert-Butyl-2-methyl-2H-pyrazol-3-yl)-3-{4-[1-(pyridin-4-yl)carbonyl-piperidin-4-yloxy]phenyl}urea | Me | 1,4-phenyl-O— | 4-Pyridinyl carbonyl | 477.1 | Ex 2 using YOH |
| 8 | 1-(5-tert-Butyl-2-methyl-2H-pyrazol-3-yl)-3-{4-[1-(cyclopentyl)carbonyl-piperidin-4-yloxy]phenyl}urea | Me | 1,4-phenyl-O— | Cyclopentyl carbonyl | 468.2 | Ex 2 using YOH |
| 9 | 1-(5-tert-Butyl-2-methyl-2H-pyrazol-3-yl)-3-{4-[1-(3-thienyl)carbonyl-piperidin-4-yloxy]phenyl}urea | Me | 1,4-phenyl-O— | 3-Thienyl-carbonyl | 482.2 | Ex 2 using YOH |
| 10 | 1-(5-tert-Butyl-2-methyl-2H-pyrazol-3-yl)-3-{4-[1-(2-chloro-6-fluorobenzoyl)-piperidin-4-yloxy]phenyl}urea | Me | 1,4-phenyl-O— | 2-Chloro-6-fluoro-benzoyl | 528.2 | Ex 2 using YOH |
| 11 | 1-(5-tert-Butyl-2-methyl-2H-pyrazol-3-yl)-3-{4-[1-(imidazol-4-yl)carbonyl-piperidin-4-yloxy]phenyl}urea | Me | 1,4-phenyl-O— | 4-Imidazolyl carbonyl | 466.2 | Ex 2 using YOH |
| 12 | 1-(5-tert-Butyl-2-methyl-2H-pyrazol-3-yl)-3-{4-[1-(pyrazol-4-yl)carbonyl-piperidin-4-yloxy]phenyl}urea | Me | 1,4-phenyl-O— | 4-Pyrazolyl carbonyl | 466.2 | Ex 2 using YOH |
| 13 | 1-(5-tert-Butyl-2-methyl-2H-pyrazol-3-yl)-3-{4-[1-(2-trifluoromethyl benzoyl)-piperidin-4-yloxy]phenyl}urea | Me | 1,4-phenyl-O— | 2-Trifluoromethyl benzoyl | 544.2 | Ex 2 using YOH |
| 14 | 1-(5-tert-Butyl-2-methyl-2H-pyrazol-3-yl)-3-{4-[1-(2-trifluoromethoxybenzoyl)-piperidin-4-yloxy]phenyl}urea | Me | 1,4-phenyl-O— | 2-Trifluoromethoxy benzoyl | 560.2 | Ex 2 using YOH |
| 15 | 1-(5-tert-Butyl-2-methyl-2H-pyrazol-3-yl)-3-{4-[1-(2-fluorobenzoyl)-piperidin-4-yloxy]phenyl}urea | Me | 1,4-phenyl-O— | 2-Fluoro benzoyl | 494.2 | Ex 2 using YOH |
| 16 | 1-(5-tert-Butyl-2-methyl-2H-pyrazol-3-yl)-3-{4-[1-(5-chlorothien-2-yl)carbonyl-piperidin-4-yloxy]phenyl}urea | Me | 1,4-phenyl-O— | 2-(5-Chloro-thienyl) carbonyl | 516.1 | Ex 2. using YOH |
| 17 | 1-(5-tert-Butyl-2-methyl-2H-pyrazol-3-yl)-3-{4-[1-(2-methoxypyridin-3-yl)carbonyl-piperidin-4-yloxy]phenyl}urea | Me | 1,4-phenyl-O— | 3-(2-Methoxy-pyridinyl) carbonyl | 507.2 | Ex 2 using YOH |

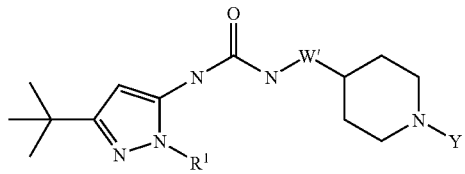

| Ex. No. | Name | R¹ | W' | Y | ES+ m/z [M + H] | Synthetic Method(s) Analogous to: |
|---|---|---|---|---|---|---|
| 18 | 1-(5-tert-Butyl-2-methyl-2H-pyrazol-3-yl)-3-{4-[1-(1-phenylcyclopropyl)carbonyl-piperidin-4-yloxy]phenyl}urea | Me | 1,4-phenyl-O— | 1-Phenyl-cyclopropyl carbonyl | 516.3 | Ex 2 using YOH |
| 19 | 1-(5-tert-Butyl-2-methyl-2H-pyrazol-3-yl)-3-{4-[1-(2-methoxypyridin-5-yl)carbonyl-piperidin-4-yloxy]phenyl}urea | Me | 1,4-phenyl-O— | 5-(2-Methoxy-pyridinyl) carbonyl | 507.2 | Ex 2 using YOH |
| 20 | 1-(5-tert-Butyl-2-methyl-2H-pyrazol-3-yl)-3-{4-[1-(2-chloropyridin-5-yl)carbonyl-piperidin-4-yloxy]phenyl}urea | Me | 1,4-phenyl-O— | 5-(2-Chloro pyridinyl) carbonyl | 511.1 | Ex 2 using YOH |
| 21 | 1-(5-tert-Butyl-2-methyl-2H-pyrazol-3-yl)-3-{4-[1-(pyrrol-3-yl)carbonyl-piperidin-4-yloxy]phenyl}urea | Me | 1,4-phenyl-O— | 3-Pyrrolyl carbonyl | 465.2 | Ex 2 using YOH |
| 22 | 1-(5-tert-Butyl-2-methyl-2H-pyrazol-3-yl)-3-{4-[1-(2-chloropyridin-3-yl)carbonyl-piperidin-4-yloxy]phenyl}urea | Me | 1,4-phenyl-O— | 3-(2-Chloro-pyridinyl) carbonyl | 511.2 | Ex 2 using YOH |
| 23 | 1-(5-tert-Butyl-2-methyl-2H-pyrazol-3-yl)-3-{4-[1-(2,6-dimethoxypyridin-3-yl)carbonyl-piperidin-4-yloxy]phenyl}urea | Me | 1,4-phenyl-O— | 3-(2,6-Di-methoxy-pyridinyl) carbonyl | 537.3 | Ex 2 using YOH |
| 24 | 1-(5-tert-Butyl-2-methyl-2H-pyrazol-3-yl)-3-{4-[1-(1,3,5-trimethylpyrazol-4-yl)carbonyl-piperidin-4-yloxy]phenyl}urea | Me | 1,4-phenyl-O— | 4-(1,3,5-Tri-methyl-pyrazolyl) carbonyl | 508.3 | Ex 2 using YOH |
| 25 | 1-(5-tert-Butyl-2-methyl-2H-pyrazol-3-yl)-3-{4-[1-(3-methylthien-2-yl)carbonyl-piperidin-4-yloxy)phenyl}urea | Me | 1,4-phenyl-O— | 2-(3-Methyl-thienyl) carbonyl | 496.2 | Ex 2 using YOH |
| 26 | 1-(5-tert-Butyl-2-methyl-2H-pyrazol-3-yl)-3-{4-[1-(3-chloro-thien-2-yl)carbonyl-piperidin-4-yloxy]phenyl}urea | Me | 1,4-phenyl-O— | 2-(3-Chloro-thienyl) carbonyl | 516.2 | Ex 2 using YOH |
| 27 | 1-(5-tert-Butyl-2-methyl-2H-pyrazol-3-yl)-3-{4-[1-(3,5-dichloropyridin-4-yl)carbonyl-piperidin-4-yloxy]phenyl}urea | Me | 1,4-phenyl-O— | 4-(3,5-Dichloro-pyridinyl) carbonyl | 545.1 | Ex 2 using YOH |
| 28 | 1-(5-tert-Butyl-2-methyl-2H-pyrazol-3-yl)-3-{5-fluoro-3-[1-(2,6-dichlorobenzoyl)-piperidin-4-yloxy]phenyl}urea | Me | ![F-substituted phenyl-O structure] | 2,6-Dichloro-benzoyl | 562.3 | Ex 1 & 2 starting with 3,5-difluoro-nitro benzene in Prep 1 |

-continued

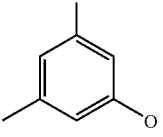

| Ex. No. | Name | R¹ | W' | Y | ES+ m/z [M + H] | Synthetic Method(s) Analogous to: |
|---|---|---|---|---|---|---|
| 29 | 1-(5-tert-Butyl-2-methyl-2H-pyrazol-3-yl)-3-{5-fluoro-3-[1-(2-chlorobenzoyl)-piperidin-4-yloxy]phenyl}urea | Me | 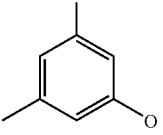 | 2-Chloro-benzoyl | 528.3 | Ex 28 using YOH |
| 30 | 1-(5-tert-Butyl-2-methyl-2H-pyrazol-3-yl)-3-{5-fluoro-3-[1-(2-trifluoromethyl benzoyl)-piperidin-4-yloxy]-phenyl}urea | Me | 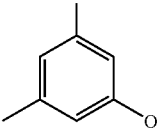 | 2-Trifluoro-methyl-benzoyl | 562.3 | Ex 28 using YOH |
| 31 | 1-(5-tert-Butyl-2-methyl-2H-pyrazol-3-yl)-3-{5-fluoro-3-[1-(2,6-difluorobenzoyl)-piperidin-4-yloxy]phenyl}urea | Me | 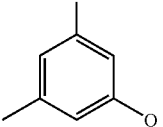 | 2,6-difluoro-benzoyl | 530.3 | Ex 28 using YOH |
| 32 | 1-(5-tert-Butyl-2-methyl-2H-pyrazol-3-yl)-3-{5-fluoro-3-[1-(2-fluorobenzoyl)-piperidin-4-yloxy]phenyl}urea | Me | 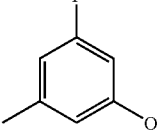 | 2-Fluoro-benzoyl | 512.3 | Ex 28 using YOH |
| 33 | 1-(5-tert-Butyl-2-methyl-2H-pyrazol-3-yl)-3-{5-fluoro-3-[1-(2-fluoro-6-chlorobenzoyl)-piperidin-4-yloxy]phenyl}urea | Me | 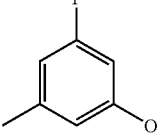 | 2-Chloro-6-fluoro-benzoyl | 546.3 | Ex 28 using YOH |
| 34 | 1-(5-tert-Butyl-2-methyl-2H-pyrazol-3-yl)-3-{5-fluoro-3-[1-(2-trifluoromethoxy benzoyl)-piperidin-4-yloxy]phenyl}urea | Me | 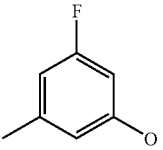 | 2-Trifluoro-methoxy-benzoyl | 578.3 | Ex 28 using YOH |
| 35 | 1-(5-tert-Butyl-2-methyl-2H-pyrazol-3-yl)-3-{5-fluoro-3-[1-(benzoyl)-piperidin-4-yloxy]phenyl}urea | Me | 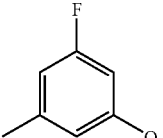 | Benzoyl | 494.3 | Ex 28 using YOH |
| 36 | 1-(5-tert-Butyl-2-methyl-2H-pyrazol-3-yl)-3-{5-fluoro-3-[1-(3-pyrrolyl)carbonyl-piperidin-4-yloxy]phenyl}urea | Me |  | 3-Pyrrolyl-carbonyl | 483.3 | Ex 28 using YOH |

-continued

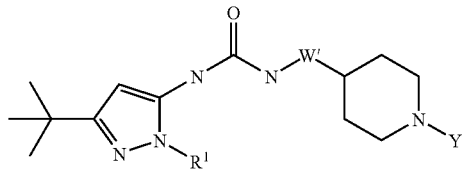

| Ex. No. | Name | R¹ | W' | Y | ES+ m/z [M + H] | Synthetic Method(s) Analogous to: |
|---|---|---|---|---|---|---|
| 37 | 1-(5-tert-Butyl-2-methyl-2H-pyrazol-3-yl)-3-[4-(1-methanesulfonyl-piperidin-4-yloxy)-phenyl]urea | Me | 1,4-phenyl-O— | Methylsulfonyl | 450.1 | From MeSO₂Cl acylation of 1-(5-tert-butyl-2-methyl-2H-pyrazol-3-yl)-3-[4-(piperidin-4-yloxy)-phenyl]-urea |
| 38 | 1-(5-tert-Butyl-2-methyl-2H-pyrazol-3-yl)-3-{4-[1-(2-chlorobenzoyl)-piperidin-4-yloxy]phenyl}urea | Me | 1,4-phenyl-O— | 2-Chloro-benzoyl | 510.1 | Ex. 3 using [4-(4-Amino-phenoxy)-piperidin-1-yl]-(2-chloro phenyl)-methanone |
| 39 | 1-(5-tert-Butyl-2-methyl-2H-pyrazol-3-yl)-3-{4-[1-(2,6-difluorobenzoyl)-piperidin-4-yloxy]phenyl}urea | Me | 1,4-phenyl-O— | 2,6-Difluoro-benzoyl | 512.1 | Ex. 3 using [4-(4-Amino-phenoxy)-piperidin-1-yl]-(2,6-difluoro phenyl)-methanone |
| 40 | 1-(5-tert-Butyl-2-p-tolyl-2H-pyrazol-3-yl)-3-{4-[1-(2,6-dichlorobenzoyl)-piperidin-4-yloxy]phenyl}urea | p-tolyl | 1,4-phenyl-O— | 2,6-Dichloro-benzoyl | 621.9 | Ex. 3 using (5-tert-butyl-2-tolyl-2H-pyrazol-3-yl)-carbamic acid 2,2,2-trichloro-ethyl ester |
| 41 | 1-(5-tert-Butyl-2-p-tolyl-2H-pyrazol-3-yl)-3-{4-[1-(cyclopropyl)carbonyl-piperidin-4-yloxy]phenyl}urea | p-tolyl | 1,4-phenyl-O— | Cyclopropyl carbonyl | 516.1 | Ex. 40 using [4-(4-Amino-phenoxy)-piperidin-1-yl]-(cyclo-propyl)-methanone |
| 42 | 1-(5-tert-Butyl-2-p-tolyl-2H-pyrazol-3-yl)-3-{4-[1-(2,6-dichlorobenzoyl)-piperidin-4-yloxy]-1-naphthyl}-urea. | p-tolyl | 1,4-naphthyl-O— | 2,6-Dichloro-benzoyl | 670.2 | Ex. 40 using [4-(4-Amino-naphthyl-oxy)-piperidin-1-yl]-(2,6-dichloro-phenyl)-methanone |
| 43 | 1-(5-tert-Butyl-2-p-tolyl-2H-pyrazol-3-yl)-3-{4-[1-(2,6-dichlorobenzoyl)-piperidin-4-ylmethoxy]-naphthyl}-urea. | p-tolyl | 1,4-naphthyl-OCH₂— | 2,6-Dichloro benzoyl | 684.2 | Ex. 42 using [4-(4-Amino-naphthyl-oxymethyl)-piperidin-1-yl]-(2,6-dichloro-phenyl)-methanone |
| 44 | 1-(5-tert-Butyl-2-p-tolyl-2H-pyrazol-3-yl)-3-{4-[1-(2,6-dichlorobenzoyl)-piperidin-4-ylethoxy]-naphthyl}-urea. | p-tolyl | 1,4-naphthyl-OCH₂CH₂— | 2,6-Dichloro-benzoyl | 698.3 | Ex. 42 using {4-[2-(4-Amino-naphthyloxy)ethyl]-piperidin-1-yl}-(2,6-dichloro-phenyl)-methanone |
| 45 | 1-(5-tert-Butyl-2-methyl-2H-pyrazol-3-yl)-3-{3-[1-(2,6-dichlorobenzoyl)-piperidin-4-yloxy]phenyl}urea | Me | 1,3-phenyl-O— | 2,6-Dichloro-benzoyl | 544.0 | Ex. 3 using [4-(3-Amino-phenoxy)-piperidin-1-yl]-(2,6-dichloro phenyl)-methanone |

-continued

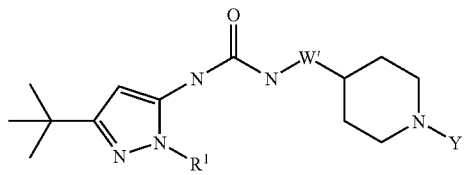

| Ex. No. | Name | R¹ | W' | Y | ES+ m/z [M + H] | Synthetic Method(s) Analogous to: |
|---|---|---|---|---|---|---|
| 46 | 1-(5-tert-Butyl-2-methyl-2H-pyrazol-3-yl)-3-{3-[1-(2-chlorobenzoyl)-piperidin-4-yloxy]phenyl}urea | Me | 1,3-phenyl-O— | 2-Chlorobenzoyl | 510.2 | Ex. 2 using YOH |
| 47 | 1-(5-tert-Butyl-2-methyl-2H-pyrazol-3-yl)-3-{3-[1-(2,6-difluorobenzoyl)-piperidin-4-yloxy]phenyl}urea | Me | 1,3-phenyl-O— | 2,6-Difluorobenzoyl | 512.3 | Ex. 2 using YOH |
| 48 | 1-(5-tert-Butyl-2-methyl-2H-pyrazol-3-yl)-3-{3-[1-(2-chloro-6-fluorobenzoyl)-piperidin-4-yloxy]phenyl}urea | Me | 1,3-phenyl-O— | 2-Chloro-6-fluoro-benzoyl | 528.2 | Ex. 2 using YOH |
| 49 | 1-(5-tert-Butyl-2-methyl-2H-pyrazol-3-yl)-3-{3-[1-(2-fluorobenzoyl)-piperidin-4-yloxy]phenyl}urea | Me | 1,3-phenyl-O— | 2-Fluorobenzoyl | 494.2 | Ex. 2 using YOH |
| 50 | 1-(5-tert-Butyl-2-methyl-2H-pyrazol-3-yl)-3-{3-[1-benzoyl-piperidin-4-yloxy]phenyl}urea | Me | 1,3-phenyl-O— | Benzoyl | 476.2 | Ex. 2 using YOH |
| 51 | 1-(5-tert-Butyl-2-methyl-2H-pyrazol-3-yl)-3-{3-[1-(2-trifluoromethyl benzoyl)-piperidin-4-yloxy]phenyl}urea | Me | 1,3-phenyl-O— | 2-Trifluoromethyl-benzoyl | 544.2 | Ex. 2 using YOH |
| 52 | 1-(5-tert-Butyl-2-methyl-2H-pyrazol-3-yl)-3-{3-[1-(2-trifluoromethoxybenzoyl)-piperidin-4-yloxy]phenyl}urea | Me | 1,3-phenyl-O— | 2-Trifluoro-methoxy-benzoyl | 560.2 | Ex. 2 using YOH |
| 53 | 1-(5-tert-Butyl-2-methyl-2H-pyrazol-3-yl)-3-{3-[1-(3-pyrrolyl)carbonyl-piperidin-4-yloxy]phenyl}urea | Me | 1,3-phenyl-O— | 3-Pyrrolyl carbonyl | 465.2 | Ex. 2 using YOH |
| 54 | 1-(5-tert-Butyl-2-methyl-2H-pyrazol-3-yl)-3-{3-[1-(benzyloxy)carbonyl-piperidin-4-yloxy]phenyl}urea | Me | 1,3-phenyl-O— | Benzyloxy-carbonyl | 506.3 | Ex. 3 using 4-(3-Amino-phenoxy)-piperidin-1-yl-carboxylic acid benzyl ester |
| 55 | 1-(5-tert-Butyl-2H-pyrazol-3-yl)-3-{4-[1-(2,6-dichlorobenzoyl)-piperidin-4-yloxy]phenyl}urea | H | 1,4-phenyl-O— | 2,6-Dichlorobenzoyl | 530.0 | Ex. 3 using 3-tert-Butyl-5-(222-trichloro-ethoxy-carbonyl-amino)-pyrazol-1-yl-carboxylic acid tert-butyl ester |
| 56 | 1-(5-tert-Butyl-2H-pyrazol-3-yl)-3-{4-[1-(2,6-difluorobenzoyl)-piperidin-4-yloxy]phenyl}urea | H | 1,4-phenyl-O— | 2,6-Difluorobenzoyl | 498.2 | Ex. 55 using [4-(4-amino-phenoxy)-piperidin-1-yl]-(2,6-difluoro-phenyl)-methanone |
| 57 | 1-(5-tert-Butyl-2H-pyrazol-3-yl)-3-{4-[1-(2-chlorobenzoyl)-piperidin-4-yloxy]phenyl}urea | H | 1,4-phenyl-O— | 2-Chloro-benzoyl | 496.1 | Ex. 55 using [4-(4-amino-phenoxy)-piperidin-1-yl]-(2-chloro-phenyl)-methanone |

-continued

| Ex. No. | Name | R¹ | W' | Y | ES+ m/z [M + H] | Synthetic Method(s) Analogous to: |
|---|---|---|---|---|---|---|
| 58 | 1-(5-tert-Butyl-2-methyl-2H-pyrazol-3-yl)-3-{3-[1-(2,6-dichlorobenzoyl)-piperidin-4-yl]phenyl}urea | Me | 1,3-phenyl | 2,6-Dichloro-benzoyl | 528.1 | Ex. 3. using [4-(3-Amino-phenyl)-piperidin-1-yl]-(2,6-dichloro-phenyl)-methanone |
| 59 | 1-(5-tert-Butyl-2-methyl-2H-pyrazol-3-yl)-3-{3-[1-(2-chloro-benzoyl)-piperidin-4-yloxy]-4-methyl-phenyl}-urea | Me | 2-Methyl-1,5-phenyl-O— | 2-Chloro-benzoyl | 524.3 | Ex. 3 using [4-(5-amino-2-methyl-phenoxy)-piperidin-1-yl]-(2-chloro-phenyl)-methanone |
| 60 | 1-(5-tert-Butyl-2-methyl-2H-pyrazol-3-yl)-3-{3-[1-(2-chlorobenzoyl)-piperidin-4-yloxy]-5-trifluoromethyl-phenyl}-urea | Me | 3-trifluoro-methyl-1,5-phenyl-O— | 2-Chloro-benzoyl | 578.2 | Ex 28 using YOH. Starting with 1-(5-tert-Butyl-2-methyl-2H-pyrazol-3-yl)-3-[3-(piperidin-4-yloxy)-5-trifluoromethyl-phenyl]-urea |
| 61 | 1-(5-tert-Butyl-2-methyl-2H-pyrazol-3-yl)-3-{3-[1-(2,6-difluoro-benzoyl)-piperidin-4-yloxy]-5-trifluoromethyl-phenyl}-urea | Me | 3-trifluoro-methyl-1,5-phenyl-O— | 2,6-Dichloro-benzoyl | 580.2 | Ex 60 using YOH |
| 62 | 1-(5-tert-Butyl-2-methyl-2H-pyrazol-3-yl)-3-(3-fluoro-5-{1-[4-(4-methyl-piperazin-1-ylmethyl)-benzoyl]-piperidin-4-yloxy}-phenyl)-urea | Me | (3-fluoro-5-methyl-phenoxy) | 4-(4-Methyl-piperazin-1-ylmethyl)-benzoyl | 606.4 | Ex 28 using YOH |
| 63 | 1-(5-tert-Butyl-2-methyl-2H-pyrazol-3-yl)-3-{1-[4-(2-(dimethylamino)-ethoxy)-benzoyl]-piperidin-4-yloxy}-5-fluoro-phenyl)-urea | Me | (3-fluoro-5-methyl-phenoxy) | 4-[2-(Dimethylamino)-ethoxy]-benzoyl | 581.3 | Ex 28. using 4-[2-(Dimethylamino)-ethoxy]-benzoic acid |
| 64 | 1-(5-tert-Butyl-2-methyl-2H-pyrazol-3-yl)-3-{3-fluoro-5-[1-(1H-indol-4-yl carbonyl)-piperidin-4-yloxy]-phenyl}-urea | Me | (3-fluoro-5-methyl-phenoxy) | 1H-Indol-4-yl carbonyl | 533.3 | Ex 28 using YOH |
| 65 | 1-(5-tert-Butyl-2-methyl-2H-pyrazol-3-yl)-3-{3-fluoro-5-[1-(1H-indol-5-yl carbonyl)-piperidin-4-yloxy]-phenyl}-urea | Me | (3-fluoro-5-methyl-phenoxy) | 1H-Indol-5-yl carbonyl | 533.3 | Ex 28. using YOH |

-continued

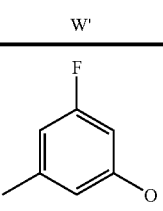

| Ex. No. | Name | R¹ | W' | Y | ES+ m/z [M + H] | Synthetic Method(s) Analogous to: |
|---|---|---|---|---|---|---|
| 66 | 1-(5-tert-Butyl-2-methyl-2H-pyrazol-3-yl)-3-{3-fluoro-5-[1-(1H-indol-7-yl carbonyl)-piperidin-4-yloxy]-phenyl}-urea | Me | 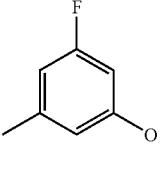 | 1H-Indol-7-yl carbonyl | 533.3 | Ex 28 using YOH |
| 67 | 1-(5-tert-Butyl-2-methyl-2H-pyrazol-3-yl)-3-{3-fluoro-5-[1-(1H-indol-2-yl carbonyl)-piperidin-4-yloxy]-phenyl}-urea | Me | 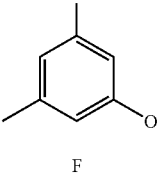 | 1H-Indol-2-yl carbonyl | 533.3 | Ex 28 using YOH |
| 68 | 1-(5-tert-Butyl-2-methyl-2H-pyrazol-3-yl)-3-{3-fluoro-5-[1-(1H-indole-3-yl carbonyl)-piperidin-4-yloxy]-phenyl}-urea | Me | 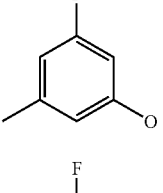 | 1H-Indol-3-yl carbonyl | 533.3 | Ex 28 using YOH |
| 69 | 1-(5-tert-Butyl-2-methyl-2H-pyrazol-3-yl)-3-{3-fluoro-5-[1-(1H-indol-6-yl carbonyl)-piperidin-4-yloxy]-phenyl}-urea | Me | 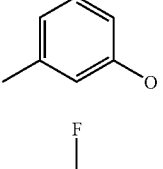 | 1H-Indol-6-yl carbonyl | 533.3 | Ex 28 using YOH |
| 70 | 1-(5-tert-Butyl-2-methyl-2H-pyrazol-3-yl)-3-{3-[1-(2,2-dimethyl-propionyl)-piperidin-4-yloxy]-5-fluoro-phenyl}-urea | Me | 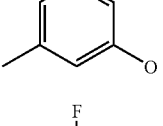 | 2,2-Dimethyl-propionyl | 474.3 | Ex 28 using YOH |
| 71 | 1-(5-tert-Butyl-2-methyl-2H-pyrazol-3-yl)-3-[3-(1-cyclopropyl-piperidin-4-yloxy)-5-fluoro-phenyl]-urea | Me | 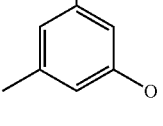 | Cyclopropyl carbonyl | 458.2 | Ex 28 using YOH |
| 72 | 1-(5-tert-Butyl-2-methyl-2H-pyrazol-3-yl)-3-{3-fluoro-5-[1-(1-methyl-cyclopropylcarbonyl)-piperidin-4-yloxy]-phenyl}-urea | Me | 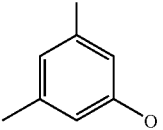 | 1-Methyl-cyclopropyl carbonyl | 472.3 | Ex 28 using YOH |
| 73 | 1-(5-tert-Butyl-2-methyl-2H-pyrazol-3-yl)-3-{3-[1-(2,2-dichloro-cyclopropylcarbonyl)-piperidin-4-yloxy]-5-fluoro-phenyl}-urea | Me | | 2,2-Dichloro-cyclopropyl carbonyl | 526.2 | Ex 28 using YOH |

-continued

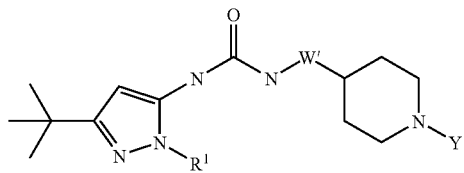

| Ex. No. | Name | R¹ | W' | Y | ES+ m/z [M + H] | Synthetic Method(s) Analogous to: |
|---|---|---|---|---|---|---|
| 74 | 1-(5-tert-Butyl-2-methyl-2H-pyrazol-3-yl)-3-{3-[1-(2,2-dichloro-1-methyl-cyclopropylcarbonyl)-piperidin-4-yloxy]-5-fluoro-phenyl}-urea | Me | (3-fluoro-5-methyl-phenyl-O) | 2,2-Dichloro-1-methyl-cyclopropyl carbonyl | 540.2 | Ex 28 using YOH |
| 75 | 1-(5-tert-Butyl-2-methyl-2H-pyrazol-3-yl)-3-{3-[1-(3-methyl-thiene-2-yl carbonyl)-piperidin-4-yloxy]-phenyl}-urea | Me | 1,4-phenyl-O— | 3-Methyl-thien-2-yl carbonyl | 496.3 | Example 2 using YOH |
| 76 | 1-(5-tert-Butyl-2-methyl-2H-pyrazol-3-yl)-3-{3-[1-(3-chloro-thiene-2-ly carbonyl)-piperidin-4-yloxy]-phenyl}-urea | Me | 1,4-phenyl-O— | 3-Chloro-thien-2-ylcarbonyl | 516.2 | Example 2 using YOH |
| 77 | 1-(5-tert-Butyl-2-methyl-2H-pyrazol-3-yl)-3-{3-[1-(2,6-dimethoxy-pyridin-3-yl carbonyl)-piperidin-4-yloxy]-phenyl}-urea | Me | 1,4-phenyl-O— | 1-(2,6-Dimethoxy-pyridin-3-yl)-carbonyl | 537.3 | Example 2 using YOH |
| 78 | 1-(5-tert-Butyl-2-methyl-2H-pyrazol-3-yl)-3-{3-[1-(3,5-dichloro-pyridin-4-yl carbonyl)-piperidin-4-yloxy]-phenyl}-urea | Me | 1,4-phenyl-O— | 1-(3,5-dichloro-pyridin-4-yl carbonyl | 545.3 | Example 2 using YOH |
| 79 | 1-(5-tert-Butyl-2-methyl-2H-pyrazol-3-yl)-3-{3-[1-(2-fluoro-6-methoxy-benzoyl)-piperidin-4-yloxy]-phenyl}-urea | Me | 1,4-phenyl-O— | 2-Fluoro-6-methoxy-benzoyl | 524.4 | Example 2 using YOH |
| 80 | 1-(5-tert-Butyl-2-methyl-2H-pyrazol-3-yl)-3-{3-[1-(2,5-dimethyl-1H-pyrrol-3-yl carbonyl)-piperidin-4-yloxy]-phenyl}-urea | Me | 1,4-phenyl-O— | 2,5-Dimethyl-1H-pyrrol-3-yl carbonyl | 494.4 | Example 2 using YOH |
| 81 | 1-(5-tert-Butyl-2-methyl-2H-pyrazol-3-yl)-3-{3-[1-(2,4-difluoro-benzoyl)-piperidin-4-yloxy]-phenyl}-urea | Me | 1,4-phenyl-O— | 2,4-Difluoro-benzoyl | 512.3 | Example 2 using YOH |
| 82 | 1-(5-tert-Butyl-2-methyl-2H-pyrazol-3-yl)-3-{3-[1-(5-chloro-thien-2-ly carbonyl)-piperidin-4-yloxy]-phenyl}-urea | Me | 1,4-phenyl-O— | 5-Chloro-thien-2-yl carbonyl | 516.0 | Example 2 using YOH |
| 83 | 1-{3-[1-(5-Bromo-thien-2-yl carbonyl)-piperidin-2-yloxy]-phenyl}-3-(5-tert-butyl-2-methyl-2H-pyrazol-3-yl)-urea | Me | 1,4-phenyl-O— | 5-Bromo-thien-2-yl carbonyl | 562.0 | Example 2 using YOH |
| 84 | 1-(5-tert-Butyl-2-methyl-2H-pyrazol-3-yl)-3-{3-fluoro-5-[1-(3-methyl-thien-2-yl carbonyl)-piperidin-4-yloxy]-phenyl}-urea | Me | (3-fluoro-5-methyl-phenyl-O) | 3-Methyl-thien-2-ylcarbonyl | 514.3 | Ex 28 using YOH |

-continued

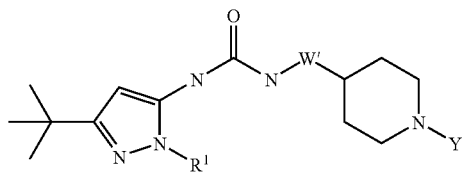

| Ex. No. | Name | R¹ | W' | Y | ES+ m/z [M + H] | Synthetic Method(s) Analogous to: |
|---|---|---|---|---|---|---|
| 85 | 1-(5-tert-Butyl-2-methyl-2H-pyrazol-3-yl)-3-{3-[1-(3-chloro-thien-2-carbonyl)-piperidin-4-yloxy]-5-fluoro-phenyl}-urea | Me | F, 3,5-substituted phenyl with O | 3-Chloro-thien-2-ylcarbonyl | 534.3 | Ex 28 using YOH |
| 86 | 1-(5-tert-Butyl-2-methyl-2H-pyrazol-3-yl)-3-{3-[1-(2,6-dimethoxy-pyridine-3-carbonyl)-piperidin-4-yloxy]-5-fluoro-phenyl}-urea | Me | F, 3,5-substituted phenyl with O | 1-(2,6-Dimethoxy-pyridin-3-yl)-carbonyl | 555.4 | Ex 28 using YOH |
| 87 | 1-(5-tert-Butyl-2-methyl-2H-pyrazol-3-yl)-3-{3-fluoro-5-[1-(2-fluoro-6-methoxy-benzoyl)-piperidin-4-yloxy]-phenyl}-urea | Me | F, 3,5-substituted phenyl with O | 2-Fluoro-6-methoxy-benzoyl | 542.4 | Ex 28 using YOH |
| 88 | 1-(5-tert-Butyl-2-methyl-2H-pyrazol-3-yl)-3-{3-[1-(2,5-dimethyl-1H-pyrrol-3-yl carbonyl)-piperidin-4-yloxy]-5-fluoro-phenyl}-urea | Me | F, 3,5-substituted phenyl with O | 2,5-Dimethyl-1H-pyrrol-3-yl carbonyl | 511.3 | Ex 28 using YOH |
| 89 | 1-(5-tert-Butyl-2-methyl-2H-pyrazol-3-yl)-3-{3-[1-(3,5-dichloro-pyridin-4-yl carbonyl)-piperidin-4-yloxy]-5-fluoro-phenyl}-urea | Me | F, 3,5-substituted phenyl with O | 1-(3,5-Dichloro-pyridin-4-yl)-carbonyl | 563.3 | Ex 28 using YOH |
| 90 | 1-(5-tert-Butyl-2-p-tolyl-2H-pyrazol-3-yl)-3-{3-fluoro-5-[1-(2-fluoro-benzoyl)-piperidin-4-yloxy]-phenyl}-urea | p-tolyl | F, 3,5-substituted phenyl with O | 2-Fluoro-benzoyl | 588.5 | Ex 1 & 2-starting with 3,5-difluoro-nitro benzene in Prep 1, and starting with (5-tert-butyl-2-tolyl-2H-pyrazol-3-yl)-carbamic acid 2,2,2-trichloro-ethyl ester in Example 1. Using YOH in Example 2 |

-continued

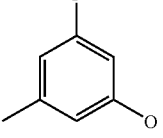

| Ex. No. | Name | R¹ | W' | Y | ES+ m/z [M + H] | Synthetic Method(s) Analogous to: |
|---|---|---|---|---|---|---|
| 91 | 1-(5-tert-Butyl-2-p-tolyl-2H-pyrazol-3-yl)-3-[3-(1-cyclopropylcarbonyl-piperidin-4-yloxy)-5-fluoro-phenyl]-urea | p-tolyl | 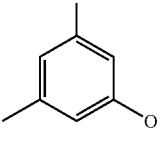 | Cyclopropyl carbonyl | 534.5 | Ex 1 & 2 starting with 3,5-difluoro-nitro benzene in Prep 1, and starting with (5-tert-butyl-2-tolyl-2H-pyrazol-3-yl)-carbamic acid 2,2,2-trichloro-ethyl ester in Example 1. Using YOH in Example 2 |
| 92 | 1-(5-tert-Butyl-2-p-tolyl-2H-pyrazol-3-yl)-3-{3-fluoro-5-[1-(3-methyl-thien-2-yl carbonyl)-piperidin-4-yloxy]-phenyl}-urea | p-tolyl | 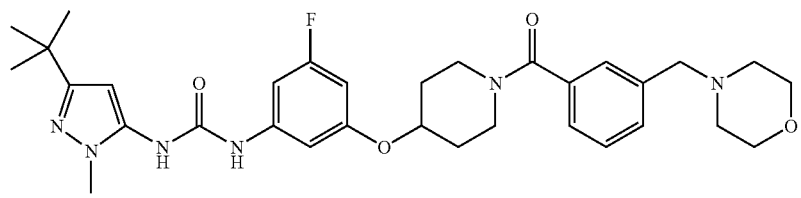 | 3-Methyl-thien-2-ylcarbonyl | 590.5 | Ex 1 & 2 starting with 3,5-difluoro-nitro benzene in Prep 1, and with (5-tert-butyl-2-tolyl-2H-pyrazol-3-yl)-carbamic acid 2,2,2-trichloro-ethyl ester in Ex 1. Using YOH in Ex 2 |

Example 93

1-(5-tert-Butyl-2-methyl-2H-pyrazol-3-yl)-3-{3-fluoro-5-[1-(3-morpholin-4-ylmethyl-benzoyl)-piperidin-4-yloxy]-phenyl}-urea A mixture of 1-(5-tert-butyl-2-methyl-2H-pyrazol-3-yl)-3-{3-fluoro-5-[3-formyl-benzoyl)-piperidin-4-yloxy]-phenyl}-urea (using Example 28, 103.9 mg, 0.2 mmol), morpholine (100 μL, 0.2 mmol), and sodium triacetoxyborohydride (96.1 mg, 0.45 mmol) in 1,2-dichloroethane (2 mL) is stirred at 22° C. overnight. Solvent is evaporated and the residue is purified on silica gel with 0-5% (2 M ammonia in methanol) in dichloromethane to give a white solid (65.3 mg, 55% yield, ES+(m/z) 593.3 [M+H]).

Example 94

4-{3-[3-(5-tert-Butyl-2-methyl-2H-pyrazol-3-yl)-ureido]-5-fluoro-phenoxy}-piperidine-1-carboxylic Acid Amide

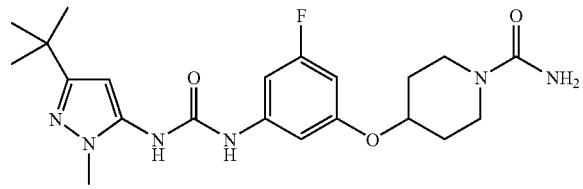

Nitrogen gas is bubbled trough a solution of 1-(5-tert-butyl-2-methyl-2H-pyrazol-3-yl)-3-{3-fluoro-5-(piperidin-4-yloxy)-phenyl}-urea (390.6 mg, 1.0 mmol) and carbamic acid phenyl ester (140.6 mg, 1.0 mmol) in DMSO (2 mL) for 5 minutes. Next, N,N-diisopropylethylamine (350 μL, 2.0 mmol) is added. After stirred at 85° C. overnight, the reaction mixture is distributed between ethyl acetate (15 mL) and saturated sodium bicarbonate (50 mL). The aqueous phase is isolated and extracted with ethyl acetate (2×15 mL). The combined organic phases are dried over sodium sulfate and concentrated. The residue is purified on a silica gel chromatography with hexanes and ethyl acetate to give a white solid (250 mg, 58% yield, ES+(m/z) 433.3 [M+H]).

Example 95

1-(5-tert-Butyl-2-methyl-2H-pyrazol-3-yl)-3-{3-fluoro-5-[1-(2,2,2-trichloro-acetyl)-piperidin-4-yloxy]-phenyl}-urea

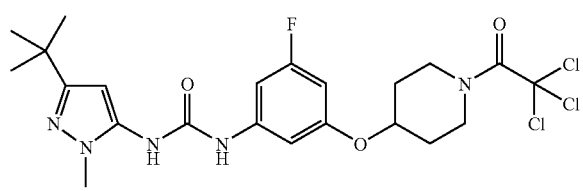

To an ice-water cooled solution of 1-(5-tert-butyl-2-methyl-2H-pyrazol-3-yl)-3-{3-fluoro-5-(piperidin-4-yloxy)-phenyl}-urea (390.6 mg, 1.0 mmol) and triethylamine (280 μL, mmol) in dichloromethane (5 mL) is added trichloroacetyl chloride (115 μL, 1.0 mmol). The reaction mixture is allowed to warm up to 22° C. and stirred for 1 hour. After removal of solvent, the residue is purified on a silica gel chromatography with hexanes and ethyl acetate to provide a white solid (520.0 mg, 97% yield, ES+(m/z) 535.9 [M+H]).

Example 96

1-(5-tert-Butyl-2-p-tolyl-2H-pyrazol-3-yl)-3-(1-(4-methylsulfonyl-benzoyl)-piperidin-4-yl)-urea

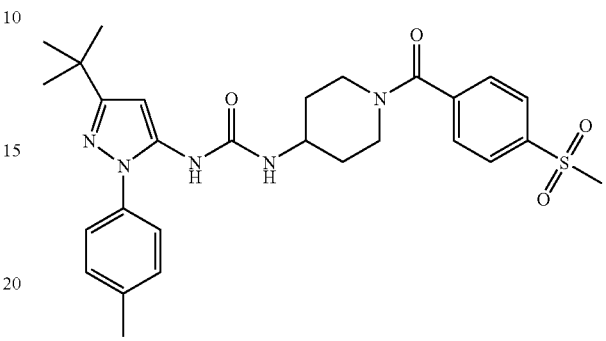

Nitrogen gas is bubbled through a solution of (4-amino-piperidin-1-yl)-(4-methylsulfonyl-phenyl)-methanone (141.6 mg, 0.50 mmol) and (5-tert-butyl-2-tolyl-2H-pyrazol-3-yl)-carbamic acid 2,2,2-trichloro-ethyl ester (204.8 mg, 0.51 mmol) in DMSO (2 mL) for 2 minutes. Next, N,N-diisopropylethylamine (0.20 mL) is added. The reaction mixture is stirred at 60° C. for 6 hours. The crude product is purified on a silica gel chromatography with ethyl acetate to give a white solid (261.2 mg, 97.2%, ES+(m/z) 538.3 [M+H]).

Example 97

1-(5-tert-Butyl-2-methyl-2H-pyrazol-3-yl)-3-{4-[4-(2,6-dichloro-benzoyl)-piperazin-1-ylmethyl]-phenyl}-urea

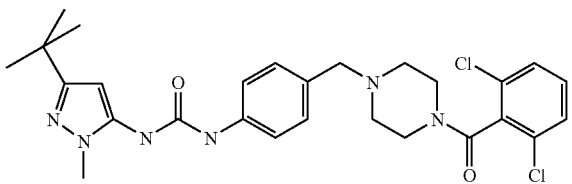

To a suspension of 75 mg (0.17 mmol) of 1-(5-tert-butyl-2-methyl-2H-pyrazol-3-yl)-3-(4-piperazin-1-ylmethyl-phenyl)-urea dihydrochloride in methylene chloride (4 mL) is added DIEA (0.103 mL, 0.6 mmol) followed by 2,6-dichlorobenzoyl chloride (0.020 mL, 0.17 mmol). The reaction mixture is stirred at room temperature overnight. Water is added (4 mL) and the organic layer separated, dried over sodium sulfate, filtered and evaporated at reduced pressure to give a pale yellow oil. The residue is chromatographed using methylene chloride to 92:8 methylene chloride:MeOH in a gradient. The title compound is collected as a white solid (30 mg; 0.06 mmol, 33%). ES+(m/z) 544 [M+H].

Using essentially the methodology of Example 97 the following examples are prepared:

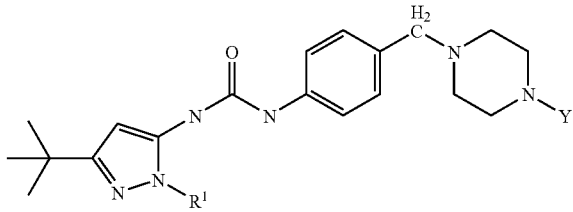

| Ex No. | Name | R¹ | Y | ES+ m/z [M + H] | Synthetic Method(s) Analogous to: |
|---|---|---|---|---|---|
| 98 | 1-(5-tert-Butyl-2-methyl-2H-pyrazol-3-yl)-3-{4-[4-acetyl-piperazin-1-ylmethyl]phenyl}urea | Me | acetyl | 413 | Ex. 97 with acetic anhydride |
| 99 | 1-(5-tert-Butyl-2-methyl-2H-pyrazol-3-yl)-3-{4-[4-(2-chlorobenzoyl)-piperazin-1-ylmethyl]phenyl}urea | Me | 2-chloro-benzoyl | 509 | Ex. 97 with 2-chlorobenzoyl chloride |
| 100 | 1-(5-tert-Butyl-2-methyl-2H-pyrazol-3-yl)-3-{4-[4-(2,6-difluorobenzoyl)-piperazin-1-ylmethyl]phenyl}urea | Me | 2,6-difluoro-benzoyl | 511 | Ex. 97 with 2,6-difluorobenzoyl chloride |
| 101 | 1-(5-tert-Butyl-2-methyl-2H-pyrazol-3-yl)-3-{4-[4-(2,4-difluoro-benzoyl)-piperazin-1-ylmethyl]-phenyl}-urea | Me | 2,4-difluoro-benzoyl | 511 | Ex. 97 with 2,4-difluorobenzoyl chloride |
| 102 | 1-(5-tert-Butyl-2-methyl-2H-pyrazol-3-yl)-3-{4-[4-(2-chloro-4-fluoro-benzoyl)-piperazin-1-ylmethyl]-phenyl}-urea | Me | 2-chloro-4-fluoro-benzoyl | 527 | Ex. 97 with 2-chloro-4-fluorobenzoyl chloride |
| 103 | 1-(5-tert-Butyl-2-methyl-2H-pyrazol-3-yl)-3-{4-[4-(2-methoxy-benzoyl)-piperazin-1-ylmethyl]-phenyl}-urea | Me | 2-methoxy-benzoyl | 505 | Ex. 97 with 2-methoxybenzoyl chloride |
| 104 | 1-[4-(4-Benzoyl-piperazin-1-ylmethyl)-phenyl]-3-(5-tert-butyl-2-methyl-2H-pyrazol-3-yl)-urea | Me | benzoyl | 475 | Ex. 97 with benzoyl chloride |
| 105 | 1-(5-tert-Butyl-2-methyl 2H-pyrazol-3-yl)-3-{4-[4-(2-chloro-6-fluoro-benzoyl)-piperazin-l-ylmethyl]-phenyl}-urea | Me | 2-chloro-6-fluoro-benzoyl | 528 | Ex. 97 with 2-chloro-6-fluoro benzoyl chloride |
| 106 | 1-(5-tert-Butyl-2-methyl-2H-pyrazol-3-yl)-3-{4-[4-(2,4-dichloro-benzoyl)-piperazin-1-ylmethyl]-phenyl}-urea | Me | 2,4-dichloro benzoyl | 545 | Ex. 97 with 2,4-dichloro benzoyl chloride |
| 107 | 1-(5-tert-Butyl-2-methyl-2H-pyrazol-3-yl)-3-{4-[4-(2,5-dichloro-thien-3-yl carbonyl)-piperazin-1-ylmethyl]-phenyl}-urea | Me | 2,5-dichloro thienyl carbonyl | 551 | Ex. 97 with 2,5-dichloro thienyl carbonyl chloride |
| 108 | 1-(5-tert-Butyl-2-methyl-2H-pyrazol-3-yl)-3-{4-[4-(4-trifluoromethyl-benzoyl)-piperazin-1-ylmethyl]-phenyl}-urea | Me | 4-trifluoro-methyl benzoyl | 544 | Ex. 97 with 4-trifluoro-benzoyl chloride |
| 109 | 1-(5-tert-Butyl-2-methyl-2H-pyrazol-3-yl)-3-{4-[4-(4-fluoro-benzoyl-piperazin-1-ylmethyl]-phenyl}-urea | Me | 4-fluoro benzoyl | 494 | Ex. 97 with 4-fluoro benzoyl chloride |

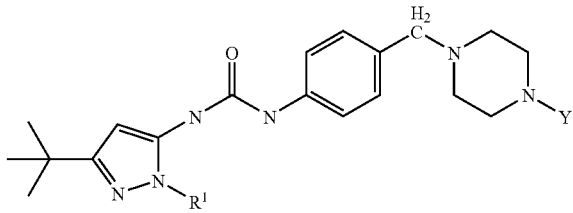

| Ex No. | Name | R¹ | Y | ES+ m/z [M + H] | Synthetic Method(s) Analogous to: |
|---|---|---|---|---|---|
| 110 | 1-(5-tert-Butyl-2-p-tolyl-2H-pyrazol-3-yl)-3-{4-[4-(2,6-difluoro-benzoyl)-piperazin-1-ylmethyl]-phenyl}-urea | p-tolyl | 2,6-difluoro-benzoyl | 588 | Ex. 97 with 2,6-di-fluoro benzoyl chloride |
| 111 | 1-(5-tert-Butyl-2-p-tolyl-2H-pyrazol-3-yl)-3-[4-(4-cyclopropylcarbonyl-piperazin-1-ylmethyl)-phenyl]-urea | p-tolyl | Cyclo-propane-carbonyl | 516 | Ex. 97 with cyclopropyl carbonyl chloride |
| 112 | 1-[4-(4-Acetyl-piperazin-1-ylmethyl)-phenyl]-3-(5-tert butyl-2-p-tolyl-2H-pyrazol-3-yl)-urea | p-tolyl | acetyl | 490 | Ex. 97 with acetic anhydride |
| 113 | 1-(5-tert-Butyl-2-p-tolyl-2H-pyrazol-3-yl)-3-{4-[4-(2,6-dichloro-benzoyl)-piperazin-1-ylmethyl]-phenyl}-urea methylsulfonate | p-tolyl | 2,6-dichloro-benzoyl | 621 | Ex. 97 with 2,6-dichloro-benzoyl chloride |
| 114 | 1-(5-tert-Butyl-2-ethyl-2H-pyrazol-3-yl)-3-{4-[4-(2,6-difluoro-benzoyl)-piperazin-1-ylmethyl]-phenyl}-urea | Ethyl | 2,6-difluoro-benzoyl | 526 | Ex. 97 with 2,6-di-fluoro benzoyl chloride |
| 115 | 1-(5-tert-Butyl-2-isopropyl 2H-pyrazol-3-yl)-3-{4-[4-(2,6-dichloro-benzoyl)-piperazin-1-ylmethyl]-phenyl}-urea | Isopropyl | 2,6-dichloro-benzoyl | 573 | Ex. 97 with 2,6-dichloro-benzoyl chloride |
| 116 | 1-(5-tert-Butyl-2-isopropyl-2H-pyrazol-3-yl)-3-{4-[4-(2,6-difluoro-benzoyl)-piperazin-1-ylmethyl]-phenyl}-urea | Isopropyl | 2,6-difluoro-benzoyl | 540 | Ex. 97 with 2,6-di-fluoro benzoyl chloride |

Using essentially the methodology of Example 97 the following examples are prepared.

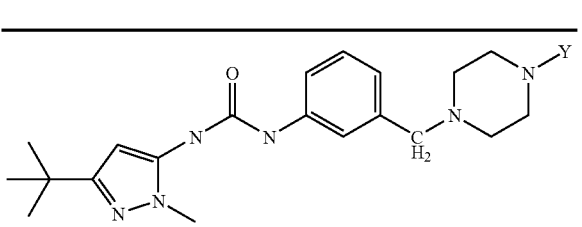

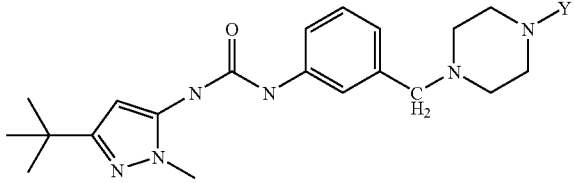

| Ex No. | Name | Y | ES+ m/z [M + H] | Synthetic Method(s) Analogous to: |
|---|---|---|---|---|
| 117 | 1-(5-tert-Butyl-2-methyl-2H-pyrazol-3-yl)-3-{3-[4-(2,6-dichloro-benzoyl)-piperazin-1-ylmethyl]-phenyl}-urea | 2,6-dichloro-benzoyl | 544 | Ex. 97 with 2,6-di-chloro-benzoyl chloride |
| 118 | 1-(5-tert-Butyl-2-methyl-2H-pyrazol-3-yl)-3-{3-[4-(2,6-difluoro-benzoyl)-piperazin-1-ylmethyl]-phenyl}-urea | 2,6-difluoro-benzoyl | 511 | Ex. 97 with 2,6-di-fluoro-chloride |

Using essentially the methodology of Example 97. The following examples are prepared:

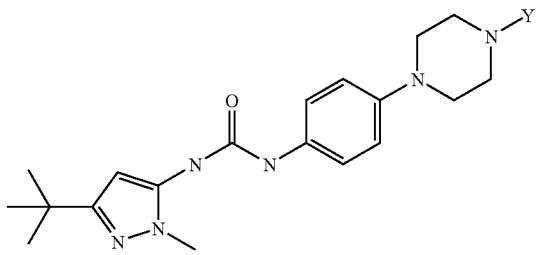

| Ex No. | Name | Y | ES+ m/z [M + H] | Synthetic Method(s) Analogous to: |
|---|---|---|---|---|
| 119 | 1-(5-tert-Butyl-2-methyl-2H-pyrazol-3-yl)-3-{4-[4-(2,6-dichloro-benzoyl)-piperazin-1-yl]-phenyl}-urea | 2,6-dichloro-benzoyl | 531 | Ex. 97 with 2,6-di chlorobenzoyl chloride. |
| 120 | 1-(5-tert-Butyl-2-methyl-2H-pyrazol-3-yl)-3-{4-[4-(2,6-difluoro-benzoyl)-piperazin-1-yl]-phenyl}-urea | 2,6-difluoro-benzoyl | 498 | Ex. 97 with 2,6-di-fluorobenzoyl chloride. |

Example 121

4-{4-[3-(5-tert-Butyl-2-p-tolyl-2H-pyrazol-3-yl)-ureido]-phenyl}-piperazine-1-carboxylic acid amide

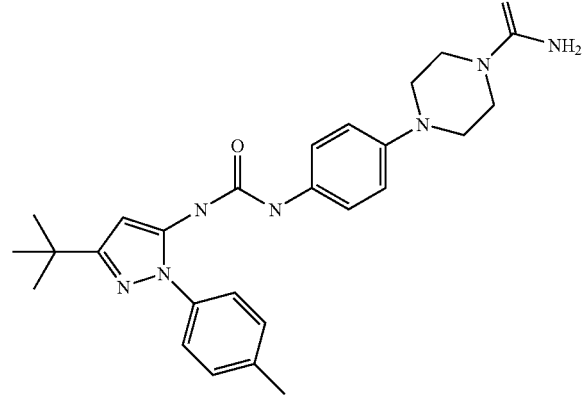

Using essentially the methodology of Example 97 but using trimethylsilyl isocyanate instead of the acid chloride, the title compound is prepared. ES+(m/z) 476 [M+H]).

Using essentially the methodology of Example 97 but using the corresponding sulfonyl chloride instead of the acid chloride, the following compounds are prepared:

| Ex No. | Name | Y | ES+ m/z [M + H] | Synthetic Method(s) Analogous to: |
|---|---|---|---|---|
| 122 | 1-(5-tert-Butyl-2-p-tolyl-2H-pyrazol-3-yl)-3-{4-[4-(prop-2-yl sulfonyl)-piperazin-1-yl]-phenyl}-urea | isopropyl-sulfonyl | 539 | Ex 97, with isopropyl-sulfonyl chloride |
| 123 | 1-(5-tert-Butyl-2-p-tolyl-2H-pyrazol-3-yl)-3-[4-(4-cyclopropyl-sulfonyl-piperazin-1-yl)-phenyl]-urea | cyclo-propyl-sulfonyl | 537 | Ex 97 with cyclo-propyl sulfonyl chloride |

Example 124

1-(5-tert-Butyl-2-p-tolyl-2H-pyrazol-3-yl)-3-{4-[4-(3,3-dimethyl-butyryl)-piperazin-1-yl]-phenyl}-urea

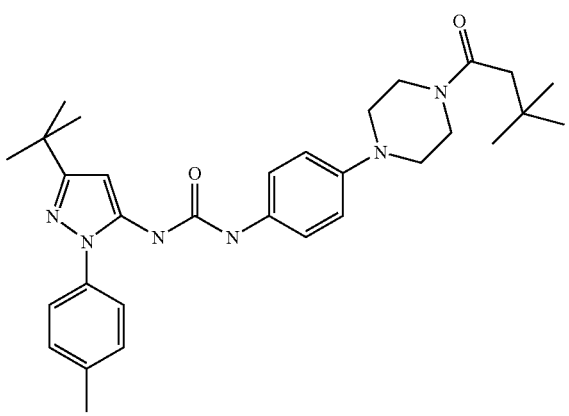

The title compound is prepared by reaction of 1-(5-tert-Butyl-2-p-tolyl-2H-pyrazol-3-yl)-3-(4-piperazin-1-yl-phenyl)-urea (0.20 g, 0.46 mmol) with 0.51 mmol of 3,3-Dimethyl-butyric acid, (0.06 g, 0.46 mmol) of 1-Hydroxybenzotriazole hydrate and (0.8 g, 0.46 mmol) of polymer supported carbodiimide, dissolved in 16 mL of $CH_2Cl_2$. Mixture is stirred at r.t.o.n. It is filtered and the resin is washed with $CH_2Cl_2$ Solvent is evaporated and the residue is purified with an SCX cartridge eluting with $NH_4OH$/$CH_3OH$ 2 N. ES+(m/z) 531 [M+H].

Using essentially the methodology of Example 124 (reaction of 1-(5-tert-Butyl-2-p-tolyl-2H-pyrazol-3-yl)-3-(4-piperazin-1-yl-phenyl)-urea with the corresponding carboxylic acid) the following compounds are prepared. In the case of the piperidine-3-carboxylic acid, reaction is carried out using the N-BOC derivative which is deprotected using HCl/dioxane 4M.

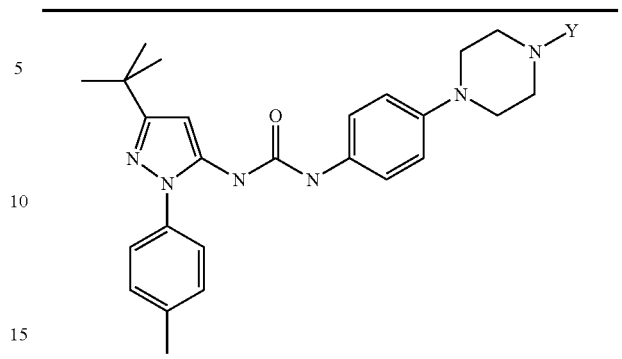

| Ex No. | Name | Y | ES+ m/z [M + H] |
|---|---|---|---|
| 125 | 1-(5-tert-Butyl-2-p-tolyl-2H-pyrazol-3-yl)-3-{4-[4-(2-cyclopentyl-acetyl)-piperazin-1-yl]-phenyl}-urea | Cyclopentyl-acetyl | 543 |
| 126 | 1-(5-tert-Butyl-2-p-tolyl-2H-pyrazol-3-yl)-3-{4-[4-(tetrahydro-fur-3-yl carbonyl)-piperazin-1-yl]-phenyl}-urea | Tetrahydro-fur-2-yl carbonyl | 531 |
| 127 | 1-(5-tert-Butyl-2-p-tolyl-2H-pyrazol-3-yl)-3-{4-[4-(1-methyl-cyclopropylcarbonyl)-piperazin-1-yl]-phenyl}-urea | 1-Methyl-cyclopropyl-carbonyl | 515 |
| 128 | 1-(5-tert-Butyl-2-p-tolyl-2H-pyrazol-3-yl)-3-{4-[4-((R)-2-methoxy-propionyl)-piperazin-1-yl]-phenyl}-urea | 2-Methoxy-propionyl | 519 |
| 129 | 1-(5-tert-Butyl-2-p-tolyl-2H-pyrazol-3-yl)-3-[4-(4-cyclobutylcarbonyl-piperazin-1-yl)-phenyl]-urea | Cyclo-butyl-carbonyl | 515 |
| 130 | 1-(5-tert-Butyl-2-p-tolyl-2H-pyrazol-3-yl)-3-{4-[4-(2,2-dimethyl-pentanoyl)-piperazin-1-yl]-phenyl}-urea | 2,2-Dimethyl-pentanoyl | 545 |
| 131 | 1-(5-tert-Butyl-2-p-tolyl-2H-pyrazol-3-yl)-3-{4-[4-(2-methyl-cyclopropylcarbonyl)-piperazin-1-yl]-phenyl}-urea | 2-Methyl-cyclopropyl-carbonyl | 515 |
| 132 | 1-(5-tert-Butyl-2-p-tolyl-2H-pyrazol-3-yl)-3-{4-[4-(piperidin-3-yl carbonyl)-piperazin-1-yl]-phenyl}-urea | Piperidin-3-yl carbonyl | 544 |

Example 133

1-(5-tert-Butyl-2-p-tolyl-2H-pyrazol-3-yl)-3-{4-[4-(2,6-difluoro-benzoyl)-piperazin-1-yl]-phenyl}-urea methylsulfonate

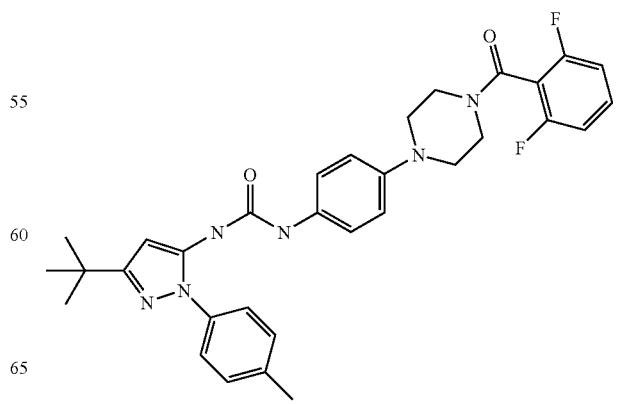

-continued

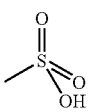

0.11 mL of 1 N solution of methylsulfonic acid in CH₂Cl₂ is added to a stirred solution of 1-(5-tert-butyl-2-p-tolyl-2H-pyrazol-3-yl)-3-{4-[4-(2,2-dimethyl-propionyl)-piperazin-1-yl]-phenyl}-urea in 1 mL of CH₂Cl₂, solution is stirred for 30 minutes. Salt solution is concentrated in vacuo. Salt is crystallized by trituration with Et₂O. The solid is filtered and dried under vacuum to give the title compound. MS(ES+H): m/z=573

Using essentially the methodology of Example 133 the following examples are prepared:

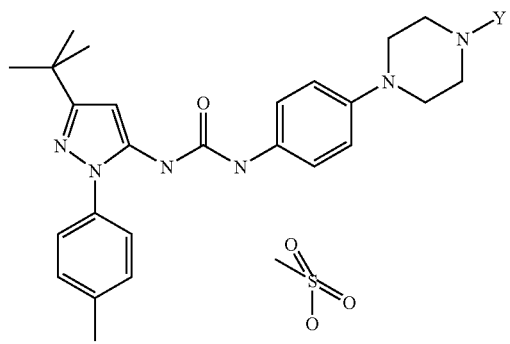

| Ex No. | Name | Y | ES+ m/z [M + H] |
|---|---|---|---|
| 134 | 1-(5-tert-Butyl-2-p-tolyl-2H-pyrazol-3-yl)-3-{4-[4-(2,6-dichloro-benzoyl)-piperazin-1-yl]-phenyl}-urea methylsulfonate | 2,6-dichloro-benzoyl | 606 |
| 135 | 1-(5-tert-Butyl-2-p-tolyl-2H-pyrazol-3-yl)-3-[4-(4-cyclopropylcarbonyl-piperazin-1-yl)-phenyl]-urea methylsulfonate | Cyclopropyl-carbonyl | 501 |
| 136 | 1-(5-tert-Butyl-2-p-tolyl-2H-pyrazol-3-yl)-3-{4-[4-(2,2-dimethyl-propionyl)-piperazin-1-yl]-phenyl}-urea methylsulfonate | tert-Butyl-carbonyl | 517 |
| 137 | 1-(5-tert-Butyl-2-p-tolyl-2H-pyrazol-3-yl)-3-[4-(4-isobutyryl-piperazin-1-yl)-phenyl]-urea methylsulfonate | i-Butyl-carbonyl] | 503 |

Example 138

1-(5-tert-Butyl-2-methyl-2H-pyrazol-3-yl)-3-{4-[4-(pyridin-4-yl carbonyl)-piperazin-1-ylmethyl]-phenyl}-urea

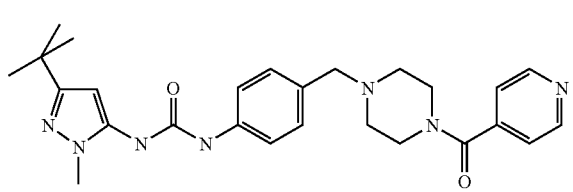

To a suspension of 75 mg (0.17 mmol) of 1-(5-tert-butyl-2-methyl-2H-pyrazol-3-yl)-3-(4-piperazin-1-ylmethyl-phenyl)-urea dihydrochloride in methylene chloride (5 mL) is added DIEA (0.103 mL, 0.6 mmol), PS-carbodiimide (266 mg, 0.34 mmol), HOBT (23 mg, 0.17 mmol) and then isonicotinic acid (21 mg, 0.17 mmol). The reaction mixture is shaken at room temperature overnight. Next, PS-trisamine (150 mg) is added and the reaction mixture shaken at room temperature for 2 hr. The mixture is filtered and evaporated to afford a yellow oil, that is chromatographed using methylene chloride to 92:8 methylene chloride:methanol in a gradient. The title compound is collected as a white solid weighing 12 mg (0.03 mmol, 18%). ES+(m/z)=476 [M+H]).

Using essentially the methodology of Example 138, the following example is prepared:

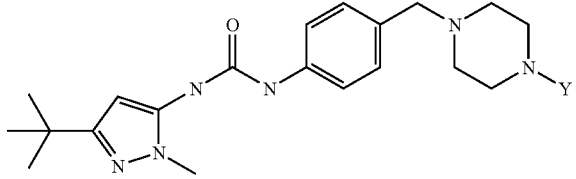

| Ex No. | Name | Y | ES+ m/z [M + H] | Synthetic Method(s) Analogous to: |
|---|---|---|---|---|
| 139 | 1-(5-tert-Butyl-2-methyl-2H-pyrazol-3-yl)-3-{4-[4-(pyridin-3-yl)carbonyl-piperazin-1-ylmethyl]phenyl}urea | 3-pyridinyl-carbonyl | 476 | Ex. 138 with nicotinic acid |

Using the method of Example 1. The following examples are prepared, wherein W' contains one of the urea nitrogens:

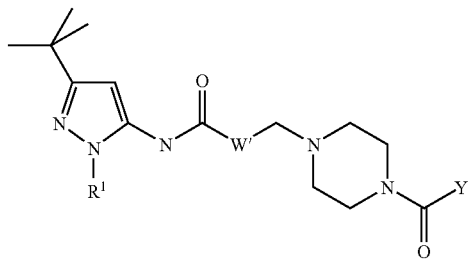

| Ex No. | Name | R₁ | W' | Y | ES+ m/z [M + H] |
|---|---|---|---|---|---|
| 140 | 1-(5-tert-Butyl-2-methyl-2H-pyrazol-3-yl)-3-{4-[4-(2,6-difluoro-benzoyl)-piperazin-1-ylmethyl]-3-fluoro-phenyl}-urea | Me | 3-F, 4-linked phenyl with HN at 1 | 2,6-difluoro-phenyl | 530 |
| 141 | 1-(5-tert-Butyl-2-methyl-2H-pyrazol-3-yl)-3-{4-[4-(2,4-difluoro-benzoyl)-piperazin-1-ylmethyl]-3-fluoro-phenyl}-urea | Me | 3-F, 4-linked phenyl with HN at 1 | 2,4-difluoro-phenyl | 530 |
| 142 | 1-(5-tert-Butyl-2-isopropyl-2H-pyrazol-3-yl)-3-{4-[4-(2,4-difluoro-benzoyl)-piperazin-1-ylmethyl]-3-fluoro-phenyl}-urea | Isopropyl | 3-F, 4-linked phenyl with HN at 1 | 2,4-difluoro-phenyl | 558 |
| 143 | 1-(2,5-Di-tert-butyl-2H-pyrazol-3-yl)-3-{4-[4-(2,6-difluoro-benzoyl)-piperazin-1-ylmethyl]-3-fluoro-phenyl}-urea | tert-Butyl | 3-F, 4-linked phenyl with HN at 1 | 2,6-difluoro-phenyl | 572 |
| 144 | 1-(5-tert-Butyl-2-methyl-2H-pyrazol-3-yl)-3-{4-[4-(2,6-difluoro-benzoyl)-piperazin-1-ylmethyl]-3-fluoro-phenyl}-urea | Me | 2-F, 4-linked phenyl with HN at 1 | 2,6-difluoro-phenyl | 530 |
| 145 | 1-(5-tert-Butyl-2-methyl-2H-pyrazol-3-yl)-3-{4-[4-(2,4-difluoro-benzoyl)-piperazin-1-ylmethyl]-3-fluoro-phenyl}-urea | Me | 2-F, 4-linked phenyl with HN at 1 | 2,4-difluoro-phenyl | 530 |
| 146 | 1-(5-tert-Butyl-2-ethyl-2H-pyrazol-3-yl)-3-{4-[4-(2,6-difluoro-benzoyl)-piperazin-1-ylmethyl]-2-fluoro-phenyl}-urea | Et | 2-F, 4-linked phenyl with HN at 1 | 2,6-difluoro-phenyl | 544 |
| 147 | 1-(5-tert-Butyl-2-ethyl-2H-pyrazol-3-yl)-3-{4-[4-(2,4-difluoro-benzoyl)-piperazin-1-ylmethyl]-2-fluoro-phenyl}-urea | Et | 2-F, 4-linked phenyl with HN at 1 | 2,4-difluoro-phenyl | 544 |
| 148 | 1-(5-tert-Butyl-2-ethyl-2H-pyrazol-3-yl)-3-{4-[4-(2,6-dichloro-benzoyl)-piperazin-1-ylmethyl]-2-fluoro-phenyl}-urea | Et | 2-F, 4-linked phenyl with HN at 1 | 2,6-dichloro-phenyl | 577 |

-continued

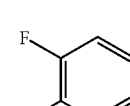

| Ex No. | Name | R₁ | W' | Y | ES+ m/z [M + H] |
|---|---|---|---|---|---|
| 149 | 1-(5-tert-Butyl-2-isopropyl-2H-pyrazol-3-yl)-3-{4-[4-(2,6-dichloro-benzoyl)-piperazin-1-ylmethyl]-2-fluoro-phenyl}-urea | Isopropyl | 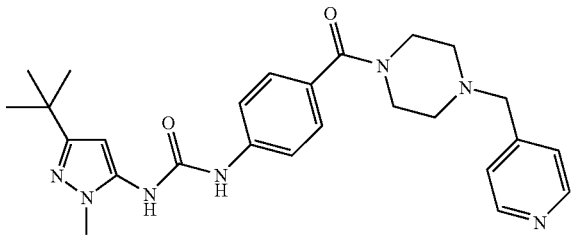 | 2,6-dichloro-phenyl | 591 |

Example 150

1-(5-tert-Butyl-2-methyl-2H-pyrazol-3-yl)-3-[4-(4-pyridin-4-ylmethyl-piperazin-1-ylcarbonyl)-phenyl]-urea

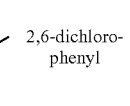

To a solution of 4-[3-(5-tert-butyl-2-methyl-2H-pyrazol-3-yl)-ureido]benzoic acid (0.08 g, 0.26 mmol) in a mixture of dichloromethane (4 mL) and DMF (0.20 mL) is added 1-(4-pyridinylmethyl)piperazine (0.046 g, 0.26 mmol), PS-DCC (0.41 g, 0.52 mmol) and HOBT (0.035 g, 0.26 mmol). The mixture is stirred overnight at 45° C. in a closed tube (orbital stirring). Then PS-Trisamine is added (0.52 mmol) and the mixture is stirred for 4 hr at room temperature, filtrated, and washed three times with dichloromethane. The solvents are evaporated under reduced pressure and the residue is purified by biotage column chromatography (eluent: ethyl acetate/methanol 10:1) to give 0.020 g (0.04 mmol), 16% as white solid. ES+(m/z)=476 [M+H].

Inhibition of p38 Kinase

Standard Solution Preparations

The kinase buffer solution is prepared by combining 2.5 mL 1M Tris-HCl (pH 7.5), 0.1 mL 1M dithiothreitol, 1.0 mL 1M magnesium chloride, and 300 µL 1% Triton X-100 and diluting to 100 mL with water. 84 mL of this kinase buffer solution is combined with 16 mL DMSO to prepare the 16% DMSO solution.

The 200 µM ATP solution is prepared by adding 102.6 µL 10 mM aqueous ATP, 25 µL ³³P-ATP, and 163.5 µL of 4 mM aqueous Epidermal Growth Factor Peptide 661-681 (Biomol, Catalog #P-121) in 5 mL kinase buffer solution.

The p38 kinase enzyme solution is prepared by dissolving 9.5 µL concentrated enzyme solution (250 ng p38 enzyme/µL kinase buffer solution) in 1536 µL kinase buffer solution.

Sample Preparation

An 80 µM solution of each test compound and control compound are prepared by dissolving 2 µL of a 10 mM stock solution of the respective compounds in dimethylsulfoxide in 248 µL of the 16% DMSO solution in a Costar 96-well microtiter plate. The plate is placed onto the Tecan Genesis automated liquid handler for 1:3 serial dilutions.

Assay

10 µL of serially diluted compound is placed with a Beckman Multimek 96-well automated liquid handler to the assay plate. 20 µL of 200 µM ATP solution is added with a Titertek Multidrop 8-channel liquid handler. 10 µL of p38 kinase enzyme solution is transferred to the assay plate using the Multimek. The mixture is allowed to react for 40 min at 30° C. and then the reaction is stopped by adding 60 µL of freshly prepared 5% glacial AcOH with Multidrop. 80 µL of this solution is transferred to an "MAPH" plate using the Multimek. The plates are allowed to set for 30 min at room temperature and then washed/aspirated on the Titertek MAP extractor with freshly prepared 0.5% glacial AcOH (1×300 µL, 2×200 µL). The wells are blotted and 100 µL MicroScint-20 scintillation fluid (Packard Bioscience) is added with the Multidrop. The plates are allowed to sit for 30 min and counted on a PE/Wallac Microbeta Trilux scintillation counter for ³³P-isotope.

All exemplified compounds are initially tested at 10 concentrations (20 µM-1 nM using 1:3 serial dilutions). Compounds with IC₅₀ values less than 25 nM are re-tested at a starting concentration of 2 µM to 0.1 nM (1:3 serial dilutions). IC₅₀ values are calculated (IDBS ActivityBase software) for each compound using non-linear regression. All exemplified compounds were tested essentially as described above and were found to inhibit the p38 kinase enzyme with an IC₅₀ of less than 5 µM. Activity for Examples 70, 100 and 136 in this assay was 0.019, 0.010 and 0.091 µM, respectively.

Inhibition of TNF-α In Vitro

Mouse Peritoneal Macrophages 1 mL thioglycolate broth (5.0 g yeast extract, 15.0 g casitone or trypticase, 5.0 g dextrose, 2.5 g sodium chloride, 0.75 g L-cystine, 0.5 g sodium thioglycolate, 1.0 mg resazurin, and 0.75 g agar in 1.0 L distilled water) are injected into the peritoneal cavity of Balb/C female mice. At day 4 or 5 post-injection the mice are sacrificed and then injected i.p. with 4 mL RPMI-1640 medium (BioWhittaker) and the peritoneal macrophages are withdrawn by syringe.

Cytokine Production

Mouse peritoneal microphages are counted with a hemocytometer and adjusted to $5 \times 10^5$ cells/well in 96-well plates in RPMI-1640 medium with 10% fetal bovine serum. 200 μL/well is plated in 96-well plates and the cells allowed to settle and adhere to the bottom of the well for at least 3 hr. The test compound or standard p38 kinase inhibitor is pre-treated using a series of 8 concentrations for 1 hr at 37° C. (20 μL/well). The cells are treated with a mixture of 50 ng/mL lipopolysaccharide (LPS) and 10 U/mL interferon-γ for 18 hr at 37° C. (20 μL/well). The conditioned media is harvested and assayed for TNF-α production using the Luminex procedure.

TNF-α/Luminex Detection Assay (Bio-Rad Bio-Plex Kit—Catalog #171-G12221)

The lyophilized premixed TNF-α standard (1 standard tube/two 96-well plates) is reconstituted with 50 μL sterile water (500,000 pg/mL). The samples are vortexed for 5 seconds, incubated on ice for 30 min, and vortexed for 5 seconds before use. A set of twelve 1.5 mL tubes are labeled with #1-thru #12 and then the amounts of cell media shown below added to the appropriate tubes (standard concentrations are as follows: 50,000; 25,000; 12,500; 6,250; 3,125; 1,562.5; 781.3; 390.6; 195.3; 97.7; 48.8; and 24.4 pg/mL). The premixed anti-cytokine conjugated beads are vortexed (25×) vigorously for 30 seconds. The anti-cytokine conjugated beads are diluted to a 1× concentration using 1× Bio-Plex Assay Buffer. For every plate, 240 μL of the pre-mixed beads is added to 5760 μL of Bio-Plex Assay Buffer. A Millipore 96-well filter plate is blocked with 100 μL/well of blocking buffer. The blocking buffer is filtered through using a Millipore filtration system and then toweled dry. 2 washes are performed on the filter plate with 100 μL/well of Bio-Plex Assay Buffer and toweled dry. The 1× anti-cytokine conjugated beads are vortexed for 15 seconds and added 50 μL to each well. This is filtered through and toweled dry. 2 washes are performed on plates with 100 μl/well of Bio-Plex Wash Buffer. Again, it is filtered through and toweled dry. 50 μL of sample or standard is added to each sample well. This is incubated for 60 seconds at room temperature on a shaker protected from light at setting 6 and then for 30 min at setting 3 and then placed in the refrigerator overnight. 3 washes are performed with Bio-Plex Wash Buffer. Filter through and toweled dry. The cytokine detection antibody is prepared (~10 min prior to use) for every plate and 60 μL of the premixed cytokine detection antibody stock is added to 5940 μL of Bio-Plex Detection Antibody Diluent.

50 μL of cytokine detection antibody is added and incubated for 60 seconds at room temperature on a shaker protected from light at setting 6 and then for 30 min at setting 3.3 washes are performed with the Bio-Plex Wash Buffer. This is filtered through and toweled dry. Strept-PE (~10 minutes prior to use) is prepared for every plate and 60 μL to 5940 μL of Bio-Plex Assay Buffer added. 50 μL of Streptavidin-PE is added to each well and incubated for 60 seconds at room temperature on a shaker protected from light at setting 6 and then for 10 min at setting 3. 3 washes are performed with Bio-Plex Wash Buffer. This is filtered through. The beads are re-suspended in 100 μL/well of Bio-Plex Assay Buffer. Standards and samples are read on a Luminex machine. These intensity readings are then converted to picogram/milliliter units based on a 12-point standard curve created in duplicate using a four-parameter logistic regression method (Bio-Plex Manager 2.0, Bio-Rad), and the $IC_{50}$ calculated.

Representative members of the exemplified compounds were tested essentially as described above and suppressed TNF-α in vitro with an $IC_{50}$ less than 100 nM. Example 100 showed an IC50=11 nM in this assay.

Inhibition of TNF—In Vivo

Compounds are administered p.o. (30, 10, 3 and 1 mg/kg) to female Balb/c mice (6 mice/dose). 1 hr following compound administration at 4 doses (P.O. at volume of 0.1 mL/mouse; vehicle: 1% NaCMC/0.25% Tween-80 in water); mice are given an IP-injection of LPS at 400 ug/kg. 1.5 hrs after LPS challenging, mice are anesthetized with isoflurane and blood is taken via cardiac puncture. TNFa-levels in the plasma are determined using ELISA kit from R&D Systems and dose response ED50 is determined.

Representative members of the exemplified compounds were tested essentially as described above and suppressed TNF—in vivo with an ED50 less than 30 mg/kg. Example 100 showed a TMED50=2.4 mg/Kg in this assay.

Effect on Intra-Articular LPS Induced TNF-α

Intra-articular injection of LPS into rat ankles induces the synthesis of TNF-α, which can be measured in synovial lavage fluid. High levels of TNF-α are detectable within 2 hours. Since the joint is the site where arthritis develops, this model can rapidly determine whether an orally administered compound has an effect on an inflammatory response in the synovium.

Six female Lewis rats (150-200 g) are place in each treatment group. The animals are given vehicle (1% NaCarboxymethylcellulose-0.25% Tween 80) or test compound (1 mg/kg, 3 mg/kg, 10 mg/kg, and 30 mg/kg) orally. One hour later, 10 μl LPS (10 μg) is administered intra-articularly into the right ankle of each rat, while the left ankle receives 10 μL of saline. After two hours, each ankle is lavaged with 100 μL of saline. The lavage is collected and stored at −80° C.

Group#1: Vehicle (1% NaCMC-0.25% Tween 80, 1 mL, PO)

Group#2: Test compound (1 mg/kg, 1 mL, PO)

Group#3: Test compound (3 mg/kg, 1 mL, PO)

Group#4: Test compound (10 mg/kg, 1 mL, PO)

Group#5: Test compound (30 mg/kg, 1 mL, PO)

TNF-α is measured with a commercially available ELISA kit (R&D, RTA00). Treatment with Example 100 produced a dose response inhibition of TNF-α synthesis, as measured in the synovial lavage fluid with ED50=30 mg/kg.

B16F10 Melanoma Target (MAPKAP-K2 Phosphorylation) and B16F10 Melanoma Metastasis Efficacy Model Inhibition of B16F10 Melanoma Lung Metastases The B16F10 melanoma cell line is obtained from the American Type Culture Collection, Rockville, Md. The cells are cultured in RPMI-1640 medium supplemented with 10% fetal calf serum. The cells grown in vitro are harvested during their exponential growth phase by gentle trypsinization, washed twice in medium, and resuspended in serum-free RPMI-1640 medium. The number of monodisperse viable cells is determined using a hemocytometer and adjusted to $1 \times 10^6$ cells/mL. Tumor cells are injected intravenously into the tail vein of normal C57B16 mice with an inoculum volume of 0.2 mL containing 200,000 cells. Mice are treated with test compound or vehicle control starting 1 day before i.v. tumor inoculation. The test compound is prepared as a suspension formulation in 1% NaCMC/0.25% polysorbate 80 and probe sonicated in an injection volume of 1% body weight (e.g., the 30 mg/kg dose level is prepared at 3 mg/mL and 0.2 cc is administered per 20 g mouse). Mice are treated orally tid. with the test compound at 30, 10, and 3 mg/kg (90, 30, and 9 mg/kg/day) from days—1 thru 16 after tumor cell inoculation. Control mice receive the vehicle alone in an identical manner. On day 16, the mice are sacrificed, and the lungs are harvested and fixed in 3% paraformaldehyde. Lung lesions are quantitated by manual counting under a dissecting microscope.

B16F10 Target (Phosphorylated MAPKAPK-2) Studies

The B16F10 melanoma cell line is obtained from the American Type Culture Collection, Rockville, Md. The cells are cultured in RPMI-1640 medium supplemented with 10% fetal calf serum. The cells grown in vitro are harvested during their exponential growth phase by gentle trypsinization, washed twice in medium, and resuspended in serum-free RPMI-1640 medium. The number of viable cells is determined using a hemocytometer and adjusted to $1 \times 10^7$/mL. Tumor cells are injected subcutaneously in normal C57B16 mice. Inoculum volume per mouse is 0.2 mL (2,000,000 cells). When the tumors reach 300-500 mg, the mice are used for target inhibition studies at either a fixed time (2.5 hours) after p.o. compound treatment or pharmacodynamic studies where the tumors are collected at multiple time-points (e.g., 3, 6, 9, 12, 15, and 18 h) after p.o. compound treatment.

Protein Extraction and Immuno-Blot Analysis

Tumors collected as described above are immediately snap-frozen in liquid nitrogen and stored at −80° C. Tumor tissues are homogenized on ice using a Daunce homogogenizer in an extraction buffer (25 mM Tris pH 7.5 containing the following protease inhibitors: 10 μg/mL leupeptin, 10 μg/mL soybean tryp-chymotrypsin inhibitor, 10 μg/mL N-tosyl-L-phenylalanine chloromethyl ketone, 10 μg/mL aprotinin, Nα-p-tosyl-L-arginine methyl ester, 7 mM benzamidine, 0.3 mM phenylmethylsulfonyl fluoride and two tablets of Roche complete protease inhibitor cocktail; following phosphatase inhibitors: 60 mM beta-glycerophosphate, 1 mM sodium vanadate, 10 mM sodium fluoride. 20 mM p-nitrophenyl phosphate, 1 μM okadaic acid, 1 μM microcystin, 2.5 mM sodium pyrophoshoate; and 1 mM dithiothreitol, 15 mM EDTA, 5 mM EGTA, 1% Triton X100 and 150 mM NaCl). Tissue lysates are cleared by centrifugation in a refrigerated microcentrifuge at 14,000 rpm and at 1° C. for 20 min. Supernatants are transferred to fresh microfuge tubes pre-chilled on ice and snap-freeze again in liquid nitrogen or dry ice. After quick thaw to about 80% completion in lukewarm water, the samples are placed on ice to complete thaw. The samples are centrifuged again at 14,000 rpm and at 1° C. for 15 min. The supernatant is transferred to fresh prechilled microfuge tubes and protein concentrations are measured using Bio-Rad protein assay reagents using bovine serum albumin as protein standard.

Protein extracts are equalized with the extraction buffer. An equal volume of 2×SDS sample buffer is added to the protein extracts and boiled in a waterbath for 5 min. 100 μg of protein extract per sample is used for electrophoresis on 4-20% gradient SDS-PAGE gel and transferred onto nitrocellulose (NC) membranes. NC membranes are blocked in 5% BSA in TBST (20 mM Tris pH=7.5, 500 mM NaCl, 0.05% Tween 20 and 0.02% sodium azide) for at least 1 hr. The membranes are then incubated in primary antibody at 1:1,000 with 5% BSA in TBST overnight on a shaker with 80 rpm at 4° C. Membranes are washed 4×, 10 min each, with TBST. The membranes are then incubated for 40 min with secondary antibody HRP (horse radish peroxidase) conjugate at 1:10,000 dilution in 3% non-fat milk in TBST and washed again 4 times with TBST, 10 min each. The immuno-blots are then visualized by enhanced chemiluminescence (ECL, Amersham) as per manufacturer's instructions. All primary antibodies are purchased from Cell Signaling and secondary antibody HRP conjugates are obtained from Amersham. Gels, membranes and apparatus used for electrophoresis and Western blotting are purchased from Invitrogen. Protein bands of interest are quantified from films using Kodak Image Station 1000.

P815 Tumor Model

Female (6-8 weeks old) DBA/2 mice (Taconic) are implanted subcutaneously into the hind flank region on day 0 with P815 cells ($0.5 \times 10^6$ cells in 200 ul of RPMI 1640). P815 tumor cells are purchased from ATCC and are cultured in RPMI 1640 medium, supplemented with glutamine and 10% bovine serum at 37° C. in 5% $CO_2$ cell culture incubator. Tumor-bearing animals are treated with oral administration of test compound at different doses or vehicle with frequency of three times a day started on the day of implantation. Tumor growth is monitored every 2 days by measuring perpendicular diameters. Tumor volume expressed in milligram (mg) is determined as the product of the largest diameter (a) and its perpendicular (b) according to the formula [tumor volume=$a \times b^2 \times 0.536$].

In Vivo Target Inhibition Study in P815 Mastocytoma Model

In vivo target inhibition is determined by measuring the effect of inhibitor treatment on the phosphorylation of MAPKAP-K2 expressed, in P815 tumor tissues. Tumors in DBA/2 mice received P815 cells subcutaneous implantation are allowed to grow to a size of 300-500 mg without treatment. Tumor bearing mice are then given oral administration of test compound or vehicle. To investigate time course related target inhibition by test compound, tumors are harvested from $CO_2$ sacrificed animals at the indicated times (3 hr, 6 hr, 12 hr, and 18 hr) after compound is dosed at 30 mg/kg. Dose-dependent target inhibition by test compound is investigated by harvesting tumors at 3 hr after orally given different doses of test compound or vehicle. Harvested tumors are immediately snap frozen onto dry ice, pulverized, homogenized and lysed in cooled lysis buffer containing proteinase and phosphatase inhibitors. After centrifugation to remove cell debris, supernatants containing 100 microgram total proteins are resuspended in 2× Tris-Glycin loading buffer and subjected to sodium dodecyl sulfate-polyacrylamide gel electrophoresis (10% Tris-Glycine) under reducing conditions. Proteins are subsequently blotted onto a PDVF membrane and were then blocked in 5% milk PBS containing 0.1% Tween-20 for 1 hr at room temperature. The membrane is then incubated with primary antibody (anti-phospho-MAPKAP-K2, Cell Signaling) at 4° C. overnight followed by incubation with secondary antibody (anti-rabbit HRP-conjugated IgG) at room temperature for 1 hr. Phospho-MAPKAP-K2 expression level is visualized by Phospho-Image detection system after the enhanced chemiluminescence (ECL) detection is used to reflect the presence of proteins on the PVDF blots. Expression level of phospho-p38 MAP kinase and total p-38 MAP kinase is also monitored by similar western blotting procedure.

Rat Collagen Induced Arthritis Efficacy Model

Female Lewis rats (≅190 g, Charles River Labs) are immunized with Bovine type II collagen (2 mg/mL) emulsified with an equal volume of adjuvant (aluminum hydroxide). are used. The rats are immunized with approximately 0.3 mg of the emulsion intradermally on the back near the base of the tail. All animals are re-immunized 7 days later according to the same protocol. The rats begin to develop arthritis (characterized by swelling and redness of one or both ankles) from 12 to 14 days after the first immunization. The rats are equally distributed into five treatment groups at the first signs of arthritis and treatment is initiated with each rat dosed bid for 14 days.

Treatment Groups:
Group 1 Vehicle (1% NaCarboxymethylcellulose+0.25% Tween 80) 1 mL, PO, Bid×14 days
Group 2 Test compound, 5 mg/kg, 1 mL, PO, Bid×14
Group 3 Test compound, 15 mg/kg, 1 mL, PO, Bid×14
Group 4 Test compound, 30 mg/kg, 1 mL, PO, Bid×14 Group 5 Prednisolone 10 mg/kg, 1 mL, PO, qd×14

Ankle diameter is measured with calipers 5 days a week and recorded. Data is expressed as the area under the curve (AUC) generated from the composite inflammation scores and statistical analysis performed.

Oral administration of the compounds of the present invention is preferred. However, oral administration is not the only route or even the only preferred route. For example, transdermal administration may be very desirable for patients who are forgetful or petulant about taking oral medicine, and the intravenous route may be preferred as a matter of convenience or to avoid potential complications related to oral administration. Compounds of Formula I may also be administered by the percutaneous, intramuscular, intranasal or intrarectal route in particular circumstances. The route of administration may be varied in any way, limited by the physical properties of the drugs, the convenience of the patient and the caregiver, and other relevant circumstances (*Remington's Pharmaceutical Sciences,* 18th Edition, Mack Publishing Co. (1990)).

The pharmaceutical compositions are prepared in a manner well known in the pharmaceutical art. The carrier or excipient may be a solid, semi-solid, or liquid material that can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solutions, suspensions, or the like.

The compounds of the present invention may be administered orally, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations of the present invention may be determined by methods well known to the skilled artisan.

The tablets, pills, capsules, troches, and the like may also contain one or more of the following adjuvants: binders such as povidone, hydroxypropyl cellulose, microcrystalline cellulose, or gelatin; excipients or diluents such as: starch, lactose, microcrystalline cellulose or dicalcium phosphate, disintegrating agents such as: croscarmellose, crospovidone, sodium starch glycolate, corn starch and the like; lubricants such as: magnesium stearate, stearic acid, talc or hydrogenated vegetable oil; glidants such as colloidal silicon dioxide; wetting agents such as: sodium lauryl sulfate and polysorbate 80; and sweetening agents such as: sucrose, aspartame or saccharin may be added or a flavoring agent such as: peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials that modify the physical form of the dosage unit, for example, as coatings. Thus, tablets or pills may be coated with sugar, hydroxypropyl methylcellulose, polymethacrylates, or other coating agents. Syrups may contain, in addition to the present compounds, sucrose as a sweetening agent and certain preservatives, dyes and colorings and flavors. Materials used in preparing these various compositions should be pharmaceutically pure and non-toxic in the amounts used.

The compounds of Formula I are generally effective over a wide dosage range.

For example, dosages per day normally fall within the range of about 0.0001 to about 30 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

We claim:
1. A compound of Formula II:

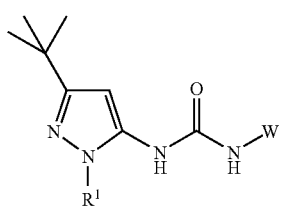

wherein:
$R^1$ is $C_1$-$C_4$ alkyl;
W is (1-Y-piperidin-4-yloxy)-phenyl-, (1-Y-piperazin-4-yl)-methyl-phenyl-, or (1-Y-piperazin-4-yl)-phenyl-, wherein phenyl is optionally substituted with one to two substituents from the group consisting of halo, methyl, and trifluoromethyl;
Y is —C(O)—$R^2$, $C_1$-$C_3$ alkylsulfonyl, or cyclopropylsulfonyl; and $R^2$ is $C_1$-$C_6$ alkyl, $C_1$-$C_6$ alkoxy, $C_1$-$C_6$ alkoxy-($C_1$-$C_6$ alkyl), amino, benzyloxy, indolyl, tetrahydrofuryl, piperidinyl, trichloromethyl, cyclopentylmethyl; $C_3$-$C_5$ cycloalkyl optionally substituted with 1-3 substituents independently selected from the group consisting of phenyl, $C_1$-$C_4$ alkyl, and halo, pyridinyl optionally substituted with 1-2 substituents independently selected from the group consisting of $C_1$-$C_4$ alkoxy and halo, thienyl optionally substituted with 1-2 halo or $C_1$-$C_4$ alkyl substituents, pyrrolyl optionally substituted with 1-2 $C_1$-$C_4$ alkyl substituents, imidazolyl, pyrazolyl optionally substituted with 1-3 $C_1$-$C_4$ alkyl substituents, or phenyl optionally substituted with 1-2 substituents independently selected from the group consisting of halo, trifluoromethyl, trifluoromethoxy, $C_1$-$C_4$ alkoxy, 4-methylpiperazin-1-ylmethyl, 2-(dimethylamino) ethoxy, and morpholin-4-ylmethyl;

or a pharmaceutically acceptable salt thereof.

2. A compound according to claim 1 wherein $R^1$ is methyl.

3. A pharmaceutical formulation comprising a compound of claim 1 in combination with a pharmaceutically acceptable carrier, diluent or excipient.

* * * * *